(12) United States Patent
Champagne et al.

(10) Patent No.: US 8,864,804 B2
(45) Date of Patent: Oct. 21, 2014

(54) BENT DIP FUSION SCREW

(76) Inventors: Lloyd P. Champagne, Phoenix, AZ (US); Jozef Zoldos, Phoenix, AZ (US)

( * ) Notice: Subject to any disclaimer, the term of this patent is extended or adjusted under 35 U.S.C. 154(b) by 148 days.

(21) Appl. No.: 13/555,933

(22) Filed: Jul. 23, 2012

(65) Prior Publication Data
US 2013/0190830 A1  Jul. 25, 2013

Related U.S. Application Data

(63) Continuation-in-part of application No. 12/372,712, filed on Feb. 17, 2009, now Pat. No. 8,597,337.

(60) Provisional application No. 61/028,791, filed on Feb. 14, 2008.

(51) Int. Cl.
| | | |
|---|---|---|
| A61B 17/04 | (2006.01) | |
| A61B 17/86 | (2006.01) | |
| A61F 2/08 | (2006.01) | |
| A61B 17/16 | (2006.01) | |
| A61B 19/00 | (2006.01) | |
| A61B 17/00 | (2006.01) | |

(52) U.S. Cl.
CPC ............ *A61B 17/863* (2013.01); *A61B 17/869* (2013.01); *A61B 17/1655* (2013.01); *A61B 17/864* (2013.01); *A61B 2019/305* (2013.01); *A61B 2017/00867* (2013.01); *A61B 17/8635* (2013.01)
USPC ............ 606/309; 606/323; 606/315; 606/316

(58) Field of Classification Search
USPC ........................ 606/62, 63, 315, 323, 329, 78; 623/21.11, 21.15, 21.19
See application file for complete search history.

(56) References Cited

U.S. PATENT DOCUMENTS

2006/0129153 A1\* 6/2006 Klaue et al. ................... 606/72

\* cited by examiner

*Primary Examiner* — Andrew Yang
(74) *Attorney, Agent, or Firm* — Snell & Wilmer LLP

(57) ABSTRACT

Devices and methods are disclosed for the fusion of joints (particularly finger joints or toe joints) in a bent (or angled) position. In certain embodiments, the device is pre-bent and inserted into the joint in its pre-bent configuration. Alternatively, the device may be configured to have a first position wherein it is bent and a second position wherein it is straight. In that case, the device is preferably straightened by inserting a K-wire through a cannula in the device, and the device can be inserted into the joint in its straight position. Once inserted, the device is permitted to move to its bent position, which moves the joint to a bent position. In one embodiment the device moves to its bent position when the K-wire is removed.

48 Claims, 29 Drawing Sheets

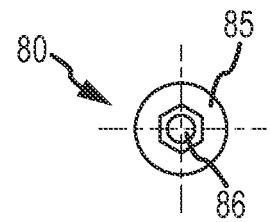
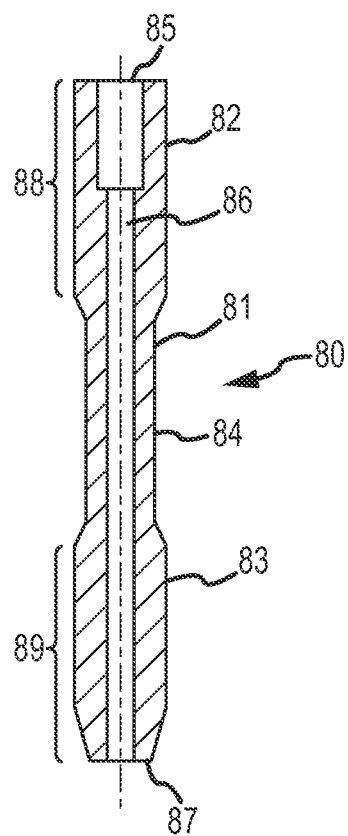
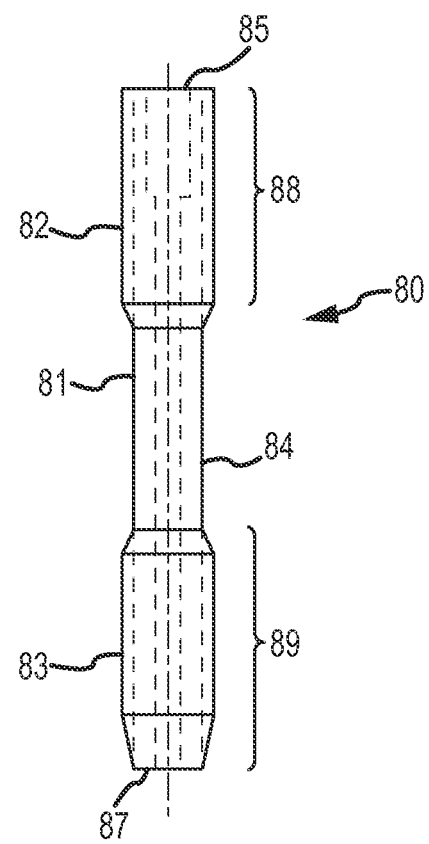
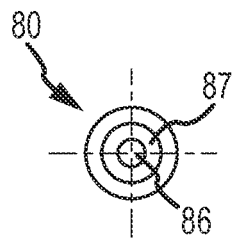

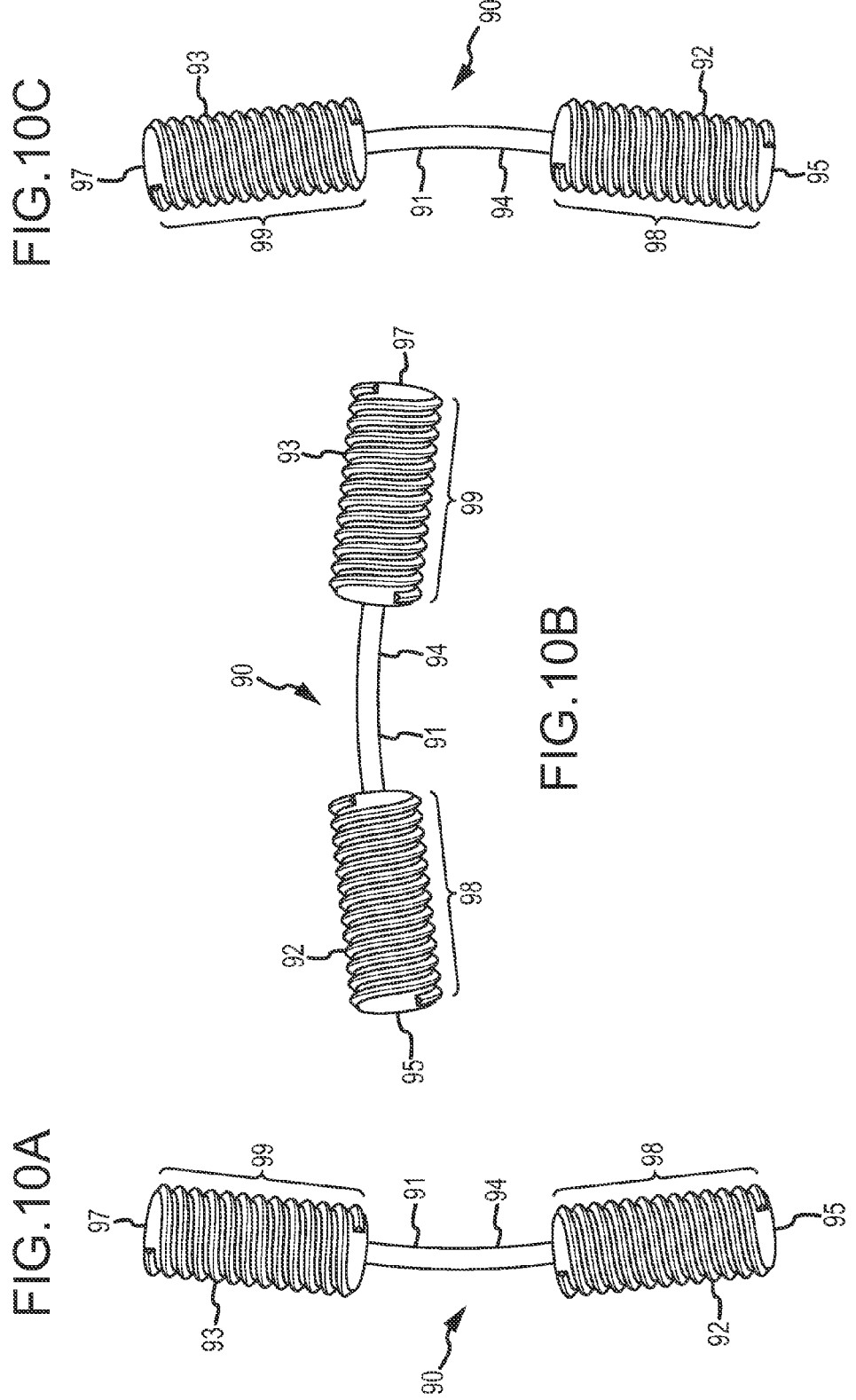

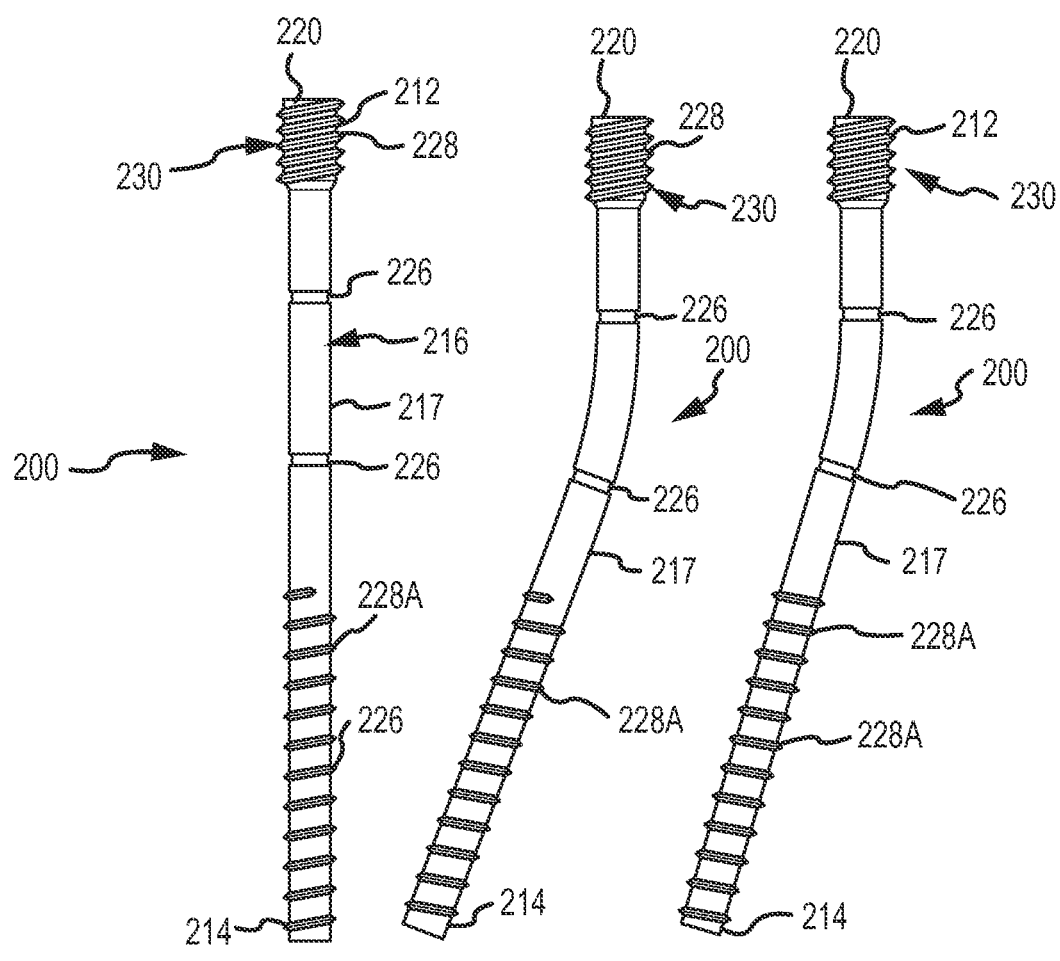

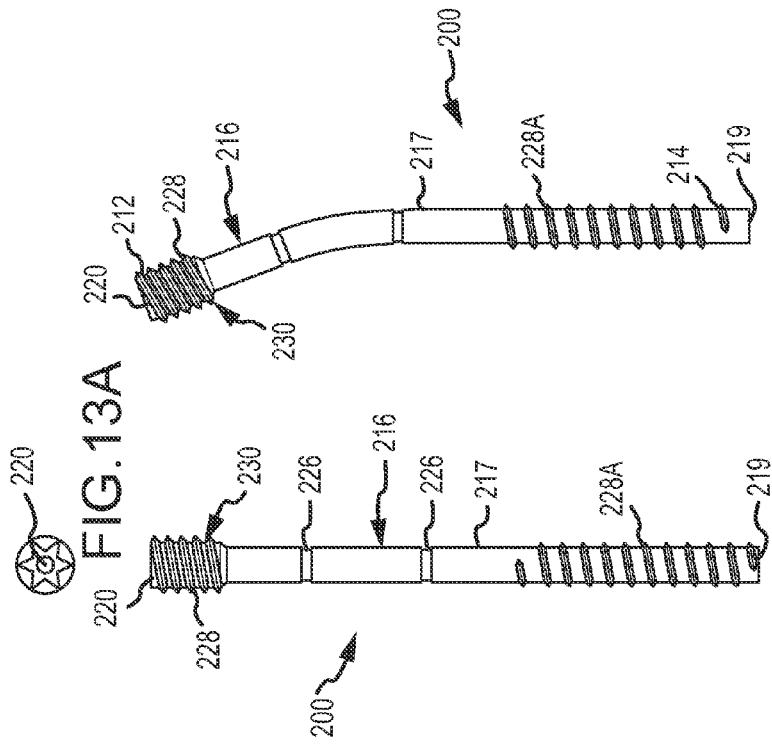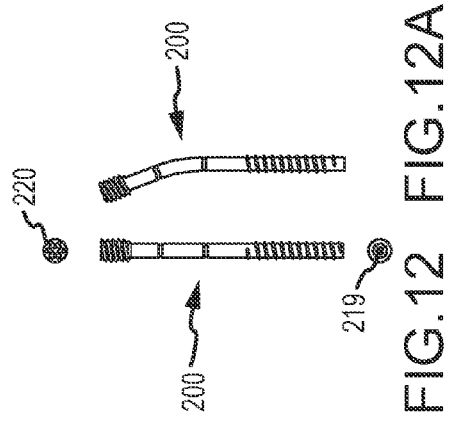

K-WIRE

K-WIRE

K-WIRE

CANNULATED DRILL

SCRUBBER TOOL

BENT DIP FUSION SCREW

CROSS REFERENCE TO RELATED APPLICATIONS

This application is a continuation in part of and claims priority to U.S. application Ser. No. 12/372,712 filed Feb. 17, 2009 and entitled "Joint Fusion Device," which claims priority to U.S. Provisional Application No. 61/028,791, filed Feb. 14, 2008.

DESCRIPTION OF THE INVENTION

1. Field of the Invention

The present invention relates to a device or method for the fusion of joints in a predetermined position.

2. Background of the Invention

The palm of the hand is made up of bones called metacarpals, and a metacarpal connects each finger and thumb to the hand. Each finger and thumb is formed of bones called phalanges. The connection of the phalanges to the metacarpals is called a "knuckle" joint or metacarpophalangeal joint (MCP joint), and acts like a hinge when the fingers or thumb are bent.

In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint.

The joints are covered on the ends with articular cartilage. Damage to the joints may occur as a result of arthritis, a sprain or fracture, and wherein the damage either directly or indirectly affects the articular cartilage. Typically, the joint does not line up the same after the injury and causes unusual wear on the articular cartilage, eventually damaging the articular surface and causing pain and loss of mobility.

Typical methods of surgically treating a damaged joint include artificial joint replacement or fusion. Fusion (arthrodesis) is used to enable bones that make up a joint to grow together into one solid bone. Fusions are commonly used in the PIP or the DIP joints in the fingers because it is easier than replacing the joint and is an acceptable alternative to replacement in many cases.

Existing methods of fusion are inadequate, such as (a) k-wire fusion, (b) or inserting a screw through the tip of the finger and through the joint to be fused because the joint is typically fused straight (i.e., without a bend in it), which is not a natural position for the joint of a finger during normal use. Herbert and Acutrack screws and their variants have been used, but by using these, the joint (DIP joint) and end of the finger are fused in a straight position, which is unnatural since the joint is normally bent during use. DIP fusions with angles can be performed but the process is technically demanding, so it is rarely performed. Additionally, the ability to angle the joint is limited and the bone purchase is poor.

Other techniques such as pin and tension band or cerclage wire do not adequately solve the problem of easily fusing a finger joint in a bent position.

SUMMARY OF THE INVENTION

It is to be understood that the descriptions of this invention herein are exemplary and explanatory only and are not restrictive of the invention as claimed.

One device for fusing joints comprises: (1) a first end, (2) a second end, (3) a middle bendable section, (4) a section between the first end and the middle bendable section that can adhere to the interior of a joint to be fused (this section is preferably threaded) wherein the outer surface between the first end and the middle bendable section preferably includes a first threaded section (or other structure for securing the section to bone), and (5) a section between the second end and the bendable middle section that can adhere to the interior of a joint to be fused (this section is preferably threaded) wherein the outer surface between the second end and the middle bendable section includes a second threaded section. The device may further include a channel or cannula therethrough to receive a support and guide structure, such as a Kirschner wire (or "K-wire").

In an alternative embodiment, removing the guide and support structure (such as a K-wire) initiates the movement of the device from a straight position to an angled position, because the device was formed in a pre-bent position and moves to the straightened position under the K-wire or other structure is positioned through the cannula. Thus, inserting the guide and support structure into the cannula initiates the movement of the device from an angled position to an approximately straight or unbent position. The support structure is removed after the device is properly anchored in the joint to be fused, which causes the device and the joint in which it is positioned to move to a bent position.

In one embodiment, the middle, bendable section can be bent at an angle of between 1 and 25 degrees. Alternatively, the middle bendable section can be bent at an angle of between 1 and 45 degrees. In yet another embodiment, the middle bendable section can be bent at an angle of between 1 and 60 degrees. The device may be between ½" and 3" long. Alternatively, it may be between ¾" and 1¾" long. In one embodiment, the device is between 1 mm to 5 mm in diameter at its thickest point. Alternatively, it may be about 3 mm in diameter at its thickest point. For larger joints, the screw may be larger.

If threads are used, the first threaded section may have a higher or otherwise different thread pitch than the second threaded section, or the first threaded section may have same thread type and pitch as the second threaded section. The device may include a self-tapping feature at the first end and a head at the second end adapted to receive an end of a driving tool, such as a screwdriver, Allen wrench or socket wrench.

The middle bendable section may be made of the same material as the rest of the device or at least part of the middle bendable section may comprise a different material than the rest of the device. In one embodiment, at least part of the first end, second end, and middle bendable section are comprised of nitinol.

In one embodiment, the middle bendable section is designed to bend in one direction. In another embodiment, the middle bendable section is designed to bend in more than one direction. The middle bendable section may comprise 20% to 75% of the device length. Alternatively, the middle bendable section may comprise 25% to 50% of the device length. In one embodiment, at least a portion of the middle bendable section has a diameter that is less than a diameter of one or more of: the diameter of part of the first end and the diameter of part of the second end. Alternatively, the middle bendable section may have the same diameter as the first section and/or second section. The device may include an orientation marker for aligning the device when placed inside a joint to enable a health care professional to know the device is in position to properly bend the finger or toe.

In any device, a feature to prevent rotation may be present. This may take the form of a ridge along all or part of the length of the device, and/or a series of nonsymmetrical features along the device to impede rotation or a texture added to the device. To achieve the same purpose the device may be square or triangular in cross section or may have features or asymmetry at the head like ridges, wings, or barbs.

Features to allow radiographic visualization of position such as notches, markers, and/or fins may be present in any embodiment. Features that control the position of a device according to the invention independent of radiographic assessment, such as clocking devices added to the screwdriver tip, may be present. Further, the screwdriver may have external marks on the handle or body that indicate the position of the device when it is inserted into a patient.

In one embodiment, between 2 and 30 lbs. of force is required to bend the middle bendable section once the device is implanted into a patient. In another embodiment, between 2 and 10 lbs. of force is required to bend the bendable section once the device is implanted into a patient.

The invention also includes a method of fusing a joint, including: (1) joining a first phalange to a first end of a device, and (2) joining a second end of the device to an adjacent phalange. The device used comprises: a shaft having a surface and comprising: the first end, the second end, a channel disposed inside the first end coupled to the second end configured to receive a support structure, and a middle bendable section. The surface between the first end and the middle bendable section may include a first threaded section, and the surface between the second end and the middle bendable section may include a second threaded section.

The method includes (1) bending the device to a determined angle, (2) inserting a support structure into the first end of the channel resulting in a reduction of the determined angle, (3) inserting the first end of the device into a bore dimensioned to accept the first end of the device, (4) orienting the device into a predetermined orientation, and (5) removing the support structure resulting in the device bending to the determined angle. In one embodiment, the reduction of the determined angle is approximately unbent. A cover may be coupled on the second end of the channel after the support structure is removed. In one embodiment, the bore for the device is dimensioned through a first phalange and the proximal end of an adjacent phalange.

In an alternate embodiment, a device according to the invention is pre-bent at an angle and anchored in its pre-bent position into the joint to be fused. Such a device is in the same in overall structure as the previously-described devices except that its middle section is pre-bent at an angle and preferably remains in that pre-bent shape while being positioned in the joint, and the angle of the bend is preferably not altered after the device is properly positioned in the joint. Additionally, the cannula for receiving a support and guiding device, such as a K-wire (hereafter, all support and guiding devices are collectively referred to as "K-wire"), in the previously summarized embodiments preferably extends through the entire device, i.e., from the first and to the second end. In this embodiment the cannula extends from a position near the distal portion of the bend to the second end. Therefore, the K-wire does not extend through the entire device, but only through a portion of the device. In this manner, as driving force is applied to a driving surface at the proximal end, the K-wire maintains the device on a relatively straight course into the joint and reduces any asymmetric movement (or wobble) caused by screwing the bent device into the joint using a driving tool. Such a device may be a one-piece or two-piece device.

BRIEF DESCRIPTION OF THE DRAWINGS

The present invention is further described in conjunction with the drawing figures:

FIGS. 8A-8D are views of an embodiment according to the present invention.

FIGS. 10A-10C are embodiments of the preset invention showing different predetermined angled configurations.

FIG. 11 is a side view of a pre-bent device according to the invention wherein the device is shown in its straightened position.

FIG. 11A is a side view of the device of FIG. 11 in its bent position.

FIG. 11B is an alternate side view of the device of FIG. 11 in its bent position.

FIG. 12 is a scale view of an embodiment the device of FIG. 11 in actual size and showing a top view of the proximal end and a bottom view of the distal end.

FIG. 12A is a side view of the device of FIG. 12 in its bent position.

FIG. 13 is an enlarged side view of the device of FIG. 12.

FIG. 13A is a top view of the proximal end of the device of FIG. 13.

FIG. 13B is a bottom view of the distal end of the device of FIG. 13.

FIG. 14 is a side view of the device of FIG. 13 in its bent position.

DESCRIPTION OF PREFERRED EMBODIMENTS OF THE INVENTION

A device or method according to the invention allows for the fusion of joints in the finger (particularly the DIP joint) in a bent (or angled) position, which is more natural when using the hand. For a finger joint, fusing the joint in a bent position also allows for the patient to be able to better grip things after a successful procedure and fusion of a joint. In certain embodiments, a device for the fusion of small hand joints preferably allows for one or more of various angled positions, and the particular angle may differ for different joints. The device is preferably a bendable screw implant for fusing together bones or a joint, and most preferably is used for fusing bones or a joint in a finger or toe.

Figure 1:
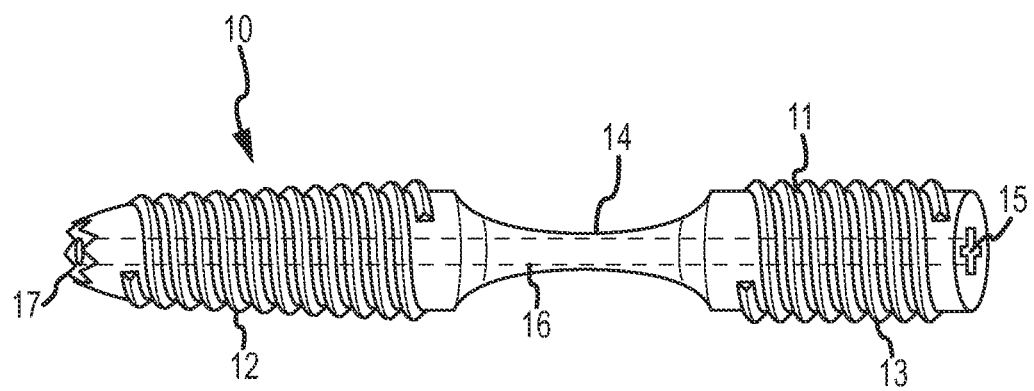
FIG. 1 is a perspective view of one embodiment according to the present invention.

With reference to FIG. 1, in one embodiment, the device is a screw 10 that has a substantially cylindrical and elongated central body 11, threaded surfaces 12, 13 approaching each end, and a bendable region 14 between threaded surfaces 12, 13. Screw 10 may have a cannula 16 as shown, which facilitates its use over a guide wire. In one embodiment, end 15 is adapted to receive a Phillips head screw driver, but any suitable adaptation is possible, such as a slotted, Torx, Pozidriv, Robertson, tri-wing, Torq-Set, Spanner Head, Triple Square, or hex configuration, or any other configuration capable of pushing or screwing the device into the body, particularly into the end of a finger or toe, in order to fuse a joint. In certain embodiments, an end of the device may be adapted to be self tapping by utilizing sharp ridges 17, but it is not limited thereto.

Figure 2:
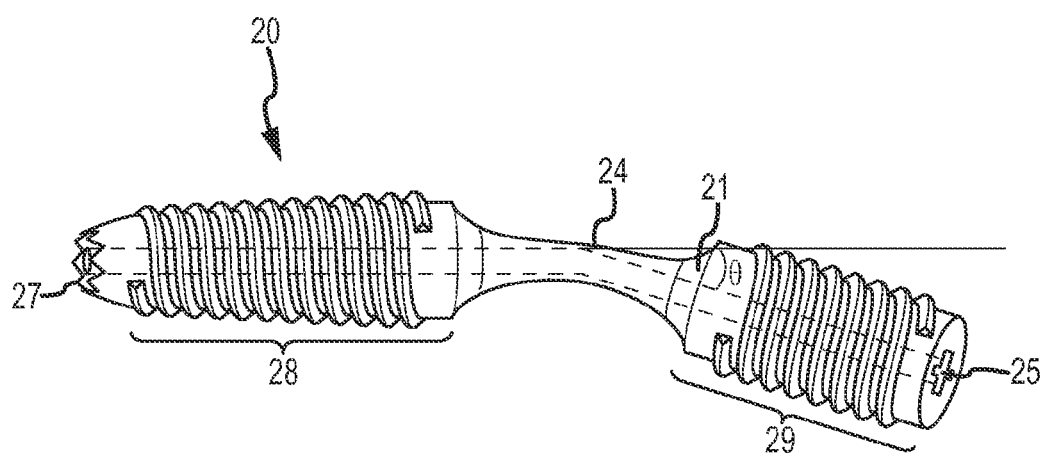
FIG. 2 is another perspective view of an angled embodiment according to the present invention.

As illustrated in FIG. 2, a device, which is shown as screw 20 (which in this case has the same configuration as screw 10) has a bendable region 24 of middle section 14. Bendable region 24 allows screw 20 to be configured for different joints by changing the angle between ends 25, 27 after the device is inserted into the body (preferably into the end of a finger). Angle 21 is formed after the device is inserted into the joint and the angle is determined according to any desired fusion position. Angle 21 could be any angle between about 5 and 70 degrees and most preferably between about 15 and 45 degrees.

Figure 3:
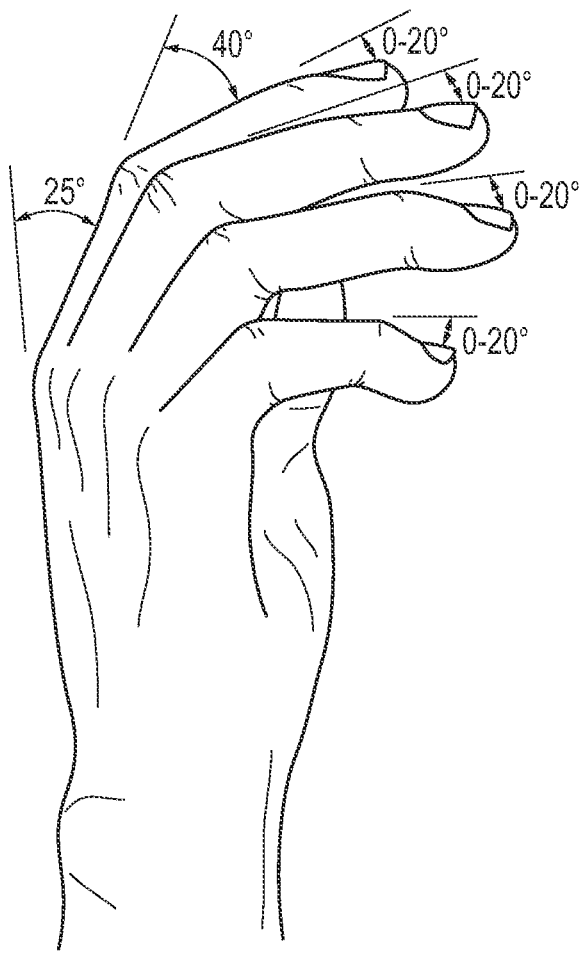
FIG. 3 illustrates optional angles for setting the different small joints in a typical hand utilizing a device according to embodiments of the invention.

FIG. 3 illustrates preferred, optimal angles for setting the different small joints in a typical hand utilizing a device according to the invention. However, different hands and different people may require different fusion angles, which can be accommodated by the invention. In some embodiments, the flexed position for the PIP or DIP joints is about 40-55 degrees, the DIP joints may vary from about 0-20 degrees, the MCP joints may vary from about 25-40 degrees, and the IP joint is typically about 20 degrees. In preferred embodiments, the angle of the device when bent is not a sharp angle, but is curved (so the bend in the bendable region, such as region 14 or region 24, is radiused or curved).

The bendable region 14 or 24 may be constructed of the same material as the rest of screw 10 or 20, and is bendable because of a reduced diameter or cross-section. In another embodiment, bendable region 14 or 24 has a different composition form the other areas of screw 10 or 20 that is more malleable, thus allowing the bendable region to bend. In preferred embodiments, bendable region 14 or 24 is bendable by a surgeon or other health-care professional after screw 10 or 20 has been inserted into the joint, and can be bent by applying between about 2 lbs. to 30 lbs. of force, and most preferably between about 2 lbs. and 10 lbs. of force. Once inserted and bent, the device is rigid enough so that ordinary use by the patient will not cause the middle bendable region to further bend or straighten out.

In some embodiments, the device material is one or more of titanium and stainless steel, but the device is not limited to these materials. The device may be comprised of any material(s) capable of fusing a finger joint, allowing the surgeon to bend the device after being inserted into a joint, and rigid enough to prevent a patient from straightening it during ordinary use.

The length of the device, such as screw 20, depends on the size of the joint and phalanges, but is preferably between ½" and 2" and most preferably between ¾" and 1½". In many embodiments, the maximum diameter of the device is the outer diameter of the highest thread, which may be between 1 mm and 5 mm, and most preferably about 3 mm. A device according to the invention may have the same diameter along its entire length, may have taper from one end to another or may have different sections with different diameters.

First threaded section 28 should be long enough and of sufficient diameter such that when inserted into a bore in a phalange, the threads grip the bone and do not allow screw 20 to twist without applying torque to end 25. Second threaded section 29 should be long enough and of sufficient diameter such that when inserted into a bore of an adjacent phalange, the threads grip the bone and do not allow screw 20 to twist. The diameter of first section 28 may taper down from bendable section 24 to first end 27. In some embodiments, the diameter of first section 28 is constant. The diameter of second section 29 may taper down from bendable section 24 to second end 25. In some embodiments, the diameter of second section 29 is constant. In further embodiments, the diameter of first section 28 is different from the diameter of second section 29.

A k-wire or pin is a sterilized, smooth stainless steel pin used in orthopedics and other types of medical applications. It comes in different sizes as needed and provide structure support, and one size has a diameter of about 0.040".

The bored hole into which the screw fits has an internal diameter that is preferably the size of the screw minus the pitch of the thread. The pitch of first section 28 may be high or low and the pitch of second section 29 may be high or low. In one embodiment, the pitch of first section 28 is high and the pitch of second section 29 is low. Sections 28 and 29 may have the same or different pitches.

Figure 4:
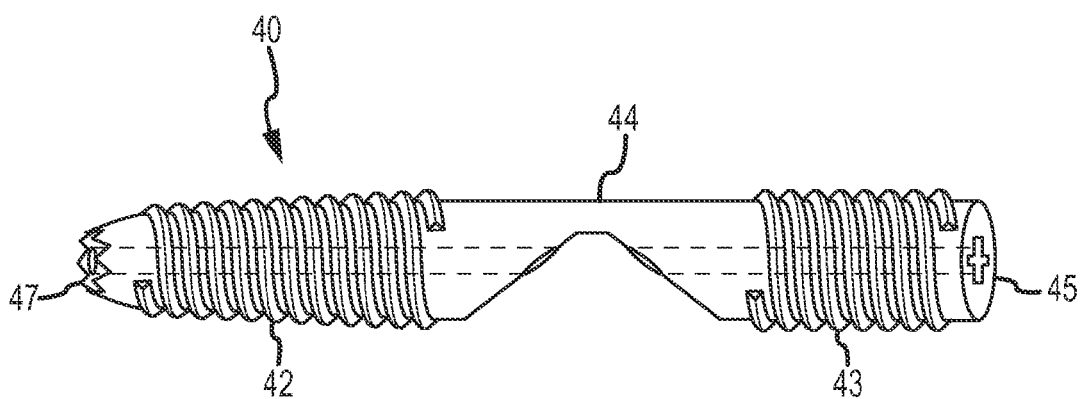
FIG. 4 is another perspective view of an angled embodiment according to the present invention.

As illustrated in FIG. 4, in some embodiments the bendable section, such as section 44, has a reduced diameter and is formed so that just one side of section 44 tapers or has reduced material. In one embodiment, bendable section 44 is created by removing material from, or not including material into, screw 40 such that a "V" shape is created in bendable section 44. Alternatively, a reduced diameter (if utilized) of bendable section 44 may be formed in any suitable manner. As previously mentioned, the bendable section may instead be comprised of a malleable material and not have a reduced diameter.

Figure 5A:
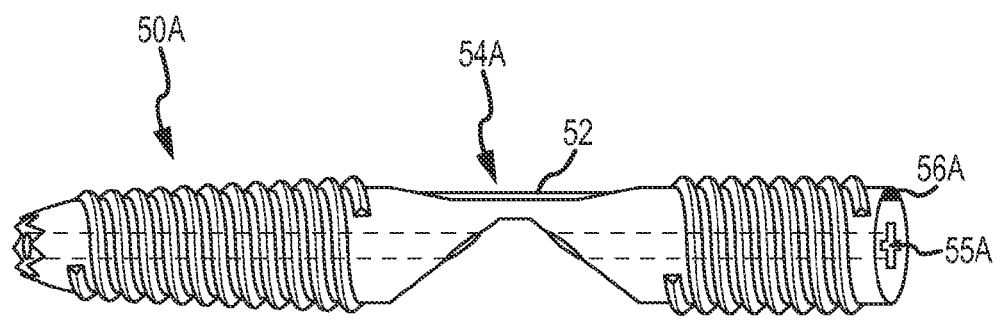
FIGS. 5A and 5B depicts embodiments of the device of FIG. 4 in operation.
Figure 5B:
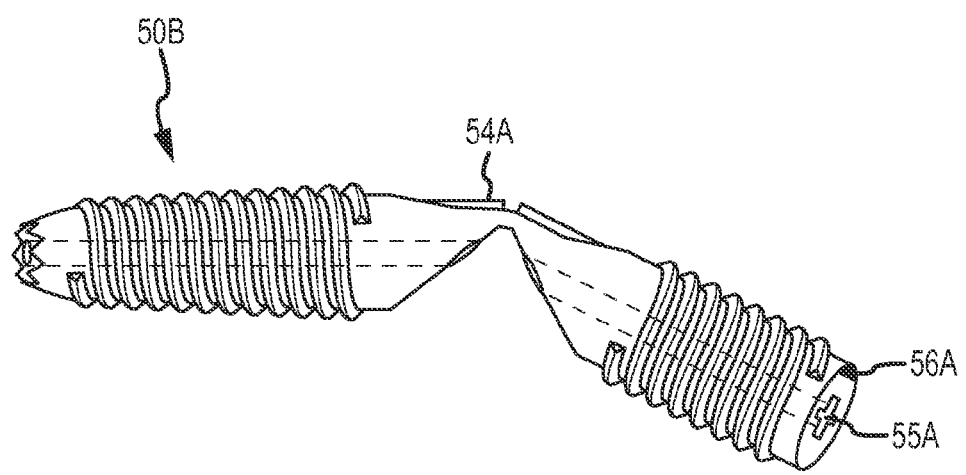

In several embodiments, and as illustrated in FIGS. 5A, B, the bendable section, such as section 44, may be prevented from bending by using a bend-back stopper 54A. In one embodiment, the bend back stopper is applied to the top surface of screw 50A where a bend is desired. Bend-back stopper 54A may be constructed of a material different from screw 50A, or may be a similar material with an optional kerf 52, thereby allowing easy bending. Upon the application of force by a surgeon, bend-back stopper 54A opens at the bend location, thereby allowing the screw to bend.

One or more orientation marks may be incorporated into the screws of the present invention. In some embodiments, as illustrated in FIGS. 5A, B, an orientation markers 56A is placed at the second end of screw 50A allowing the surgeon to know when the bending section is in the proper position relative to the first phalange and the adjacent phalange. An orientation marker is particularly useful (but not required) if the bendable middle section is designed to bend in one direction.

In one embodiment, orientation marker 56A may be an indentation stamp in the second end 55A of screw 50A or may be cast into screw end 55A or may be a mark made with a surgical marker.

Figure 6A:
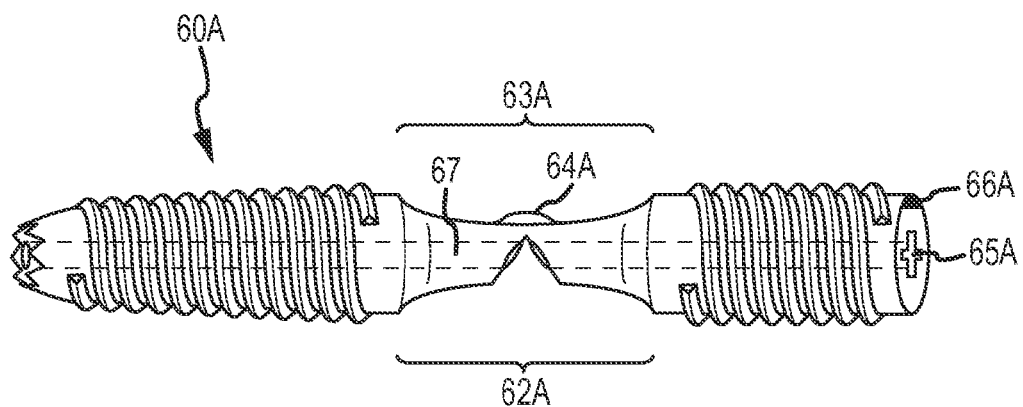
FIGS. 6A and 6B depicts embodiments of the device of FIG. 1 in operation.
Figure 6B:
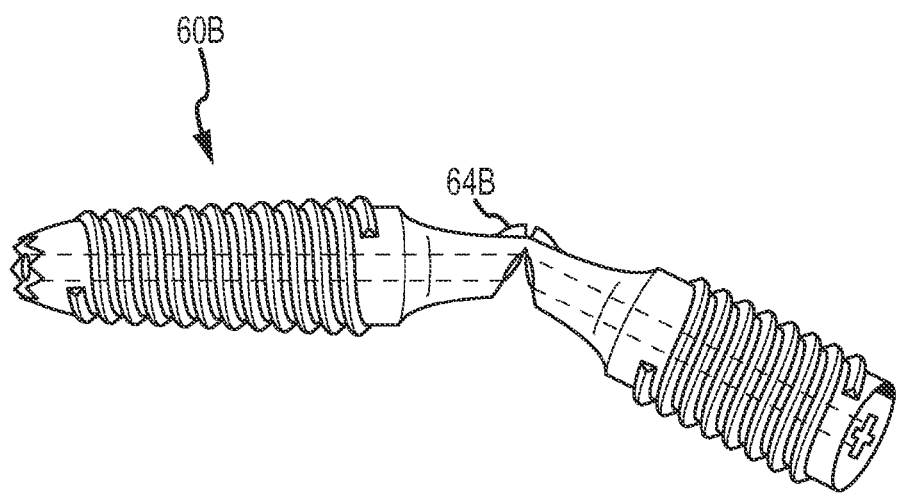

An additional embodiment of a device according to the invention is screw 60A illustrated in FIGS. 6A, B. In some embodiments, the bendable section (shown as 62A and 63A) is a reduced diameter section with the bottom bendable section 62A cutting into the cannula 67. Top bendable section 63A, which may be identified by orientation mark 66A at second end 65A, may also include a bend-back stopper 64A. Upon bending screw 60A, the bend-back stopper is separated 64B, resulting in bent screw 60B.

Figure 7:
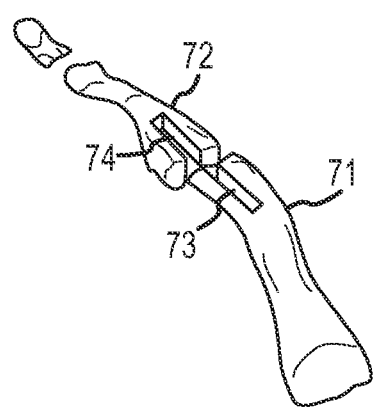
FIG. 7 illustrates one example of a PIP joint.
Figure 9A:
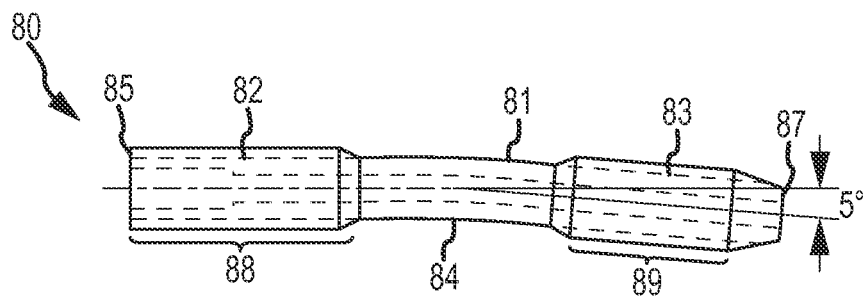
FIGS. 9A-9C are angled configurations of the embodiment shown in FIGS. 8A-8D according to the present invention.
Figure 9B:
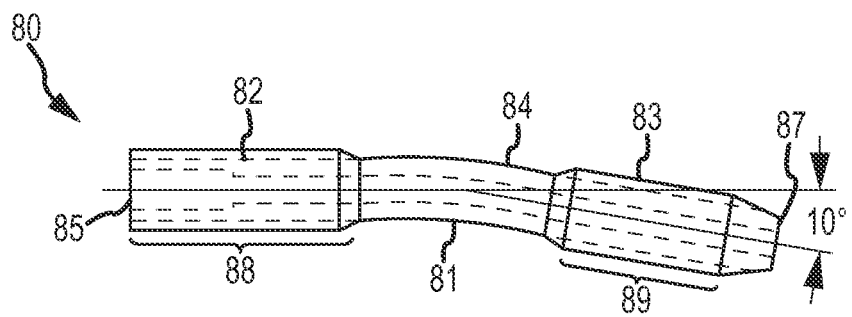
Figure 9C:
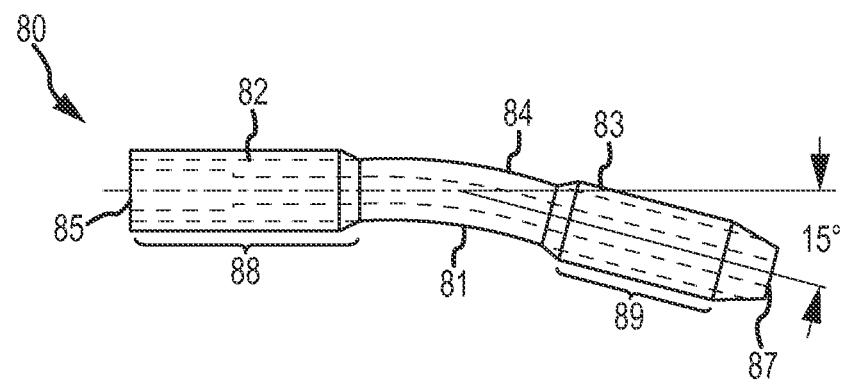

The invention also includes a method of fusing a joint using the devices disclosed herein. FIG. 7 illustrates a PIP joint, although the procedure would be similar for a DIP or MCP joint. In an embodiment as illustrated in FIG. 7, a first phalange 71 is joined to a second adjacent phalange 72 using one of the devices disclosed above. In certain embodiments, a bore 73 is provided in the distal end of a first phalange 71 and a bore 74 is provided in the proximal end of the adjacent phalange 72. A device (not shown) is preferably a screw with a first threaded end, a central bendable region, and a second threaded end is inserted into bore 73 of first phalange 71 and into bore 74 of adjacent phalange 72 using a screwdriver. Before inserting the screw into the bore of the first phalange, the bendable region may initially have zero bend, or may be pre-bent to a desired fusion angle as discussed above and shown in FIG. 3. In some embodiments, the bendable region may be bent to a desired angle after one end has been inserted into the bore of the first phalange. In other embodiments, the bendable region is bent after the second end has been placed into the bore of the adjacent phalange. In yet another embodiment, the bendable region is further bent at a later time, after the screw has been inserted.

In another embodiment for use with any of the previously-described joints (particularly joints in the fingers and toes), as shown in FIGS. 8A-8D, fusion device 80 has a substantially cylindrical and elongated central body 81, threaded surface 82, 83 near each end, and a bendable region 84 between threaded surfaces 82, 83. Screw 80 may have a channel (or cannula) 86 as shown, which may receive a support structure, such as a K-pin. The support structure may be any material strong enough to initiate the device to retract to a substantially unbent position or configuration. Channel 86 may be any suitable diameter to receive a support structure, but its diameter is preferably about 1.3 mm. Channel 86 may run the entire length of the device or it may run a portion the length of the device. Channel 86 may be a slightly larger diameter near the second end of the device (as shown in FIG. 8A) to accommodate gripping by an insertion and removal tool. In another embodiment (not shown), channel 86 may be capped at one end. This cap may run any desired length into the first end 87 and/or second end 85 of the device, and may further be integral to the device.

In one embodiment, end 85 is adapted to receive a Phillips head screw driver, but any suitable adaptation is possible, such as a slotted, Torx, Pozidriv, Robertson, tri-wing, Torq-Set, Spanner Head, Triple Square, or hex configuration, or any other configuration capable of pushing or screwing the device into the body, particularly into the end of a finger, in order to fuse a joint. In certain embodiments, an end of the device may be adapted to be self tapping by utilizing sharp ridges 87, but it is not limited thereto. As in previous embodiments, the bendable region 84 of screw 80 may be set to any desired angle such as between about 5 and 70 degrees and most preferably between about 5 and 45 degrees.

In some embodiments, the material comprising fusion device 80 is one or more of titanium, nitinol (nickel titanium), CuSn, InTi, TiNi, and MnCu and stainless steel, but the device is not limited to these materials.

Nitinol is a shape memory metal. A reversible, solid phase transformation known as martensitic transformation is the force behind shape memory alloys. The alloy material forms a crystal structure, which is capable of undergoing a change from one form of crystal structure to another. Temperature change or/and loading may initiate this transformation. A Kirschner pin is then inserted in the first end 85 of the device 80. The device 80 may be comprised of any material(s) capable of fusing a finger joint, allowing the surgeon to bend the device 80 after (and/or prior to) being inserted into a joint, and rigid enough to prevent a patient from straightening it during ordinary use. Each section may be made of different materials or they may be made of the same materials. As previously described one or more orientation marks may be incorporated into the screw of the present invention.

As previously described, screw 80 further includes a first threaded section 83 which should be long enough and of sufficient diameter such that when inserted into a bore in a phalange, the threads grip the bone and do not allow screw 80 to twist without applying torque to end 85. Second threaded section 82 should be long enough and of sufficient diameter such that when inserted into a bore of an adjacent phalange, the threads grip the bone and do not allow screw 80 to twist. These threaded sections may be made from nitinol or from a suitable different material such as stainless steel.

As show in FIGS. 8A-8D, and 9A-9C, screw 80 according to the invention may have the same diameter along its entire length, may have taper from one end to another or may have different sections with different diameters. The lead end or first end 87 of screw 80 may be shaped to assist its insertion into the phalange bore. The diameter of second section 88 may taper down from bendable section 84 to second end 85. In some embodiments, the diameter of second section 88 is constant. The diameter of first section 89 may taper down from bendable section 84 to first end 87. In some embodiments, the diameter of first section 89 is constant. Alternatively, as shown in FIGS. 8A-8D and 9A-9C, the diameter of section 89 may taper down at both ends and the diameter of second section 88 may taper down approaching bendable section 84. In further embodiments, the diameter of second section 88 is different from the diameter of first section 89.

FIGS. 10A-10C are preferred embodiments of the present invention showing different predetermined angles. A flexible tube 90 is depicted with substantially rigid collars 92, 93 coupled to either end of the tube in any suitable manner. For instance, these collars 92, 93 may be coupled to the tube using an adhesive, soldering, and/or machined from nitinol and/or integral to the tube. In this embodiment the rigid collar may be made from any suitable rigid material such as steel and/or stainless steel, hard plastic, titanium, and nitinol. The collars may be threaded 92, 93 to help secure the device in the bore dimensioned to accept the first end 97 of the device 90.

Alternatively, the collars may be barbed or formed with a deformable collar piece that is capable of holding the device in place through friction and/or pressure fit. The device 90 should remain in place once inserted for a suitable time so that the desired bones may fuse.

In the present embodiment depicted in FIGS. 10A-10C, the tube is a nitinol tube, however, any suitable material may be utilized such as titanium, CuSn, InTi, TiNi, and MnCu, other bimetals and/or stainless steel, but the device is not limited to these materials. The device 90 may be a three piece structure, or it may be a two piece or one piece structure. For instance, the device 90 may be made from many materials or as few as one material. The device 90 may be a nitinol tube with a larger collared section on either end or the tube may be approximately the same diameter as one or both of the collared ends.

As previously described, screw 90 further includes a first threaded section 93 which should be long enough and of sufficient diameter such that when inserted into a bore in a phalange, the threads grip the bone and do not allow screw 90 to twist without applying torque to end 95. Second threaded section 92 should be long enough and of sufficient diameter such that when inserted into a bore of an adjacent phalange, the threads grip the bone and do not allow screw 90 to twist. As previously described, the threads may be made from any suitable material.

Screw 90 according to the invention may have the same diameter along its entire length, may have taper from one end to another or may have different sections with different diameters. The lead end or first end 97 of screw 90 may be shaped to assist its insertion into the phalange bore. The diameter of second section 98 may taper down from bendable section 94 to second end 95. In some embodiments, the diameter of second section 98 is constant. The diameter of first section 99 may taper down from bendable section 94 to first end 97. In some embodiments, the diameter of first section 99 is constant. Alternatively, the diameter of section 99 may taper down at both ends and the diameter of second section 98 may taper down approaching bendable section 94. In further embodiments, the diameter of second section 98 is different from the diameter of first section 99.

Once the predetermined angle of the device is determined by the desired angle of bone fuse, the device is set to the predetermined angle. The predetermined angel may be zero. As depicted in FIGS. 9A-9C and 10A-10C, the angle may be set using shape memory metal such as nitinol. A support structure, such as a Kirschner pin is inserted in the channel 86 (96). This effectively straightens the predetermined angle back to an unbent position or configuration. The device 80 (90) is inserted into the bore dimensioned through a first phalange 71 and a bore 74 dimensioned in the proximal end of the adjacent phalange 72. Alternatively, a Kirschner pin may be inserted first into a patient and used as a guide for channel 86 (96) and proper insertion of the device 80 (90). The device, anchored in the phalanges, is oriented using the orientation marking on the second end 85 (95) of the device. Once the desired orientation is achieved, the Kirschner pin is removed the device 80 (90) returns to its previously predetermined bent (angled) configuration and the phalanges are bent into the predetermined angle of the device. A cap of any suitable material may be added to the second end 85 (95) once the Kirschner pin is removed if desired.

FIGS. 11-14 show a pre-bent screw (or device) 200 in accordance with an embodiment of the invention. Device 200 is a pre-bent screw, which can be pre-bent at any suitable angle, such as the angles previously described. Device 200 has a cannula therethrough (not shown) for receiving a K-wire.

Device 200 includes a first end, or proximal end, 212, and a second end, or distal end 214. Second end 214 preferably includes a cutting tip 219, which is shown in FIGS. 13, 13B and 14. First end 212 includes a driving surface 220, the preferred embodiment of which is shown in FIG. 13A. Any suitable driving surface may be used, however, including any of the driving surfaces previously described above. Cutting tip 19 narrows at the end of second tip 14 and has sharp protrusions that help it cut through any debris left inside an opening formed in the joint bones to be fused, wherein the opening is to receive device 200.

Device 200 further includes a shaft 216 having an outer surface 217, and annular gaps 226 formed in shaft 216. The annular gaps 226 have an outer diameter that is preferably smaller than the outer diameter of shaft 216 on either side of each annular gap 226. Preferably, each annular gap 226 has the same outer diameter, which is preferably about 0.5 to 1.5 mm less than the outer diameter on either side of the annular gap. The purpose of the annular gaps is to create positions at which device 200 bends, as shown in FIGS. 11A, 11B, 12A and 14. Alternatively, instead of gaps 226 device 200 may comprise a material at the location of gaps 226 that is more pliable than the material comprising the shaft around said material. This pliable material could also permit device 200 to bend.

Threads 228 and 228A are formed along shaft 216. The purpose of threads 228 and 228A is to anchor device 200 into, respectively, each bone of the joint to be fused and any suitable structure for this purpose can be used, although threads 228 and 228A are preferred. Threads 228 are formed on shaft 216 juxtaposed first end 212 and threads 228A are formed on shaft 216 juxtaposed second end 214.

Figure 15:
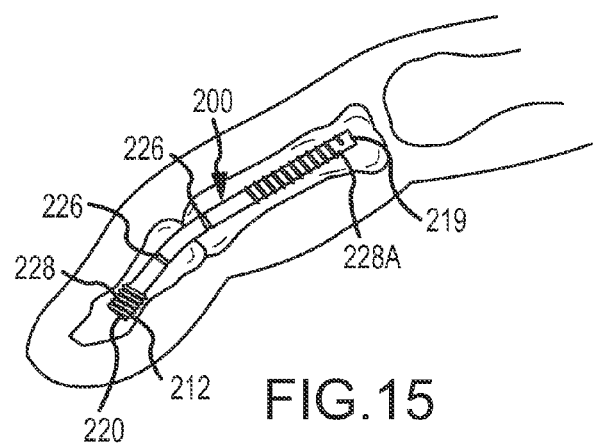
FIGS. 15 and 15A depict the device of FIG. 14 positioned in the phalange of a finger.
Figure 15A:
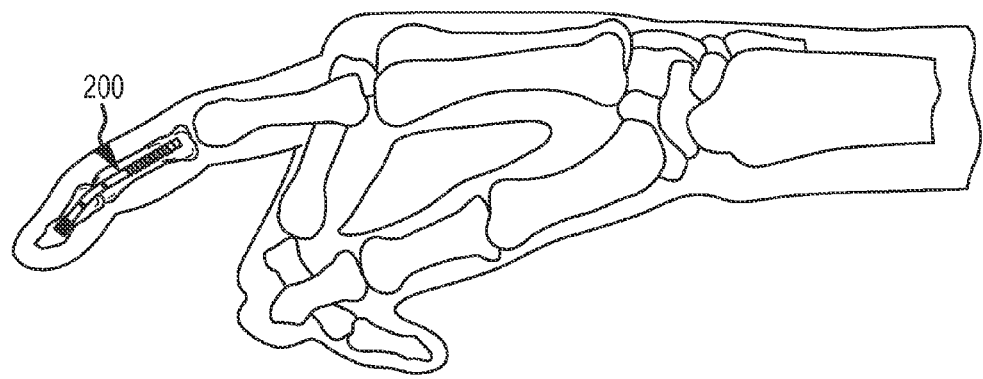

As can be seen in FIGS. 15 and 15A, once device 200 is properly positioned in a joint, threads 228A anchor device 200 into the distal joint bone and threads 228 anchor device 200 into the proximal joint bone.

Figure 16:
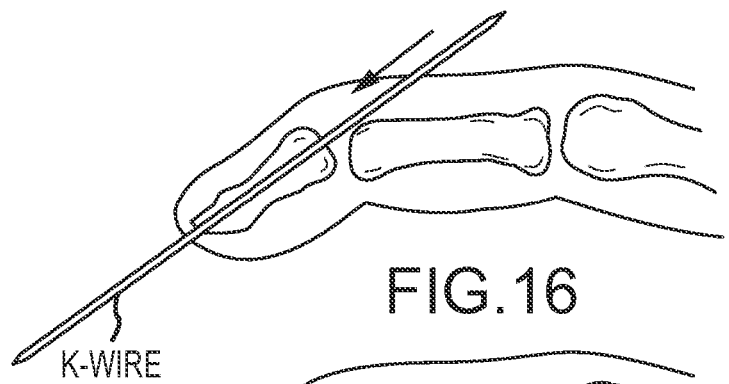
FIGS. 16-16I depict a method for positioning a device according to the invention into a finger joint.
Figure 16A:
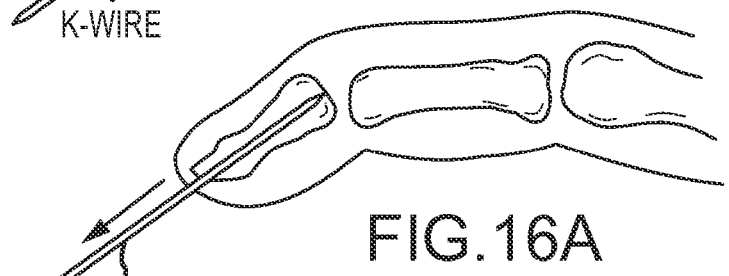
Figure 16B:
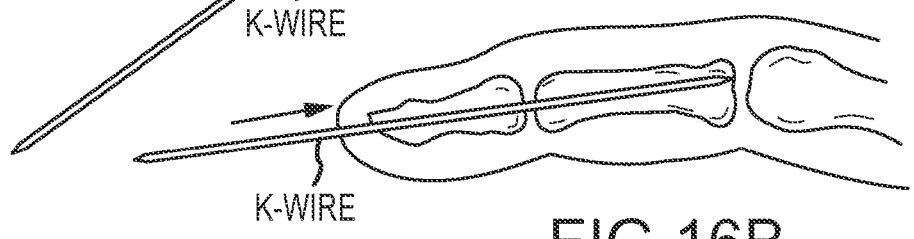

FIGS. 16-16B depict how a K-wire (or other guiding and support structure) is inserted into two bones of a joint. In this example, the K-wire is first inserted into the distal phalange. This is accomplished by angling the end of the finger and pushing the K-wire through the top of distal joint. As shown in FIG. 16A, the K-wire is pulled through the distal phalange until the distal end of the K-wire is even with the end of the distal phalange.

Figure 16C:
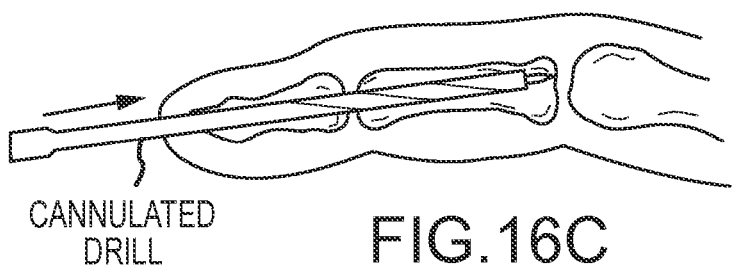
Figure 16D:
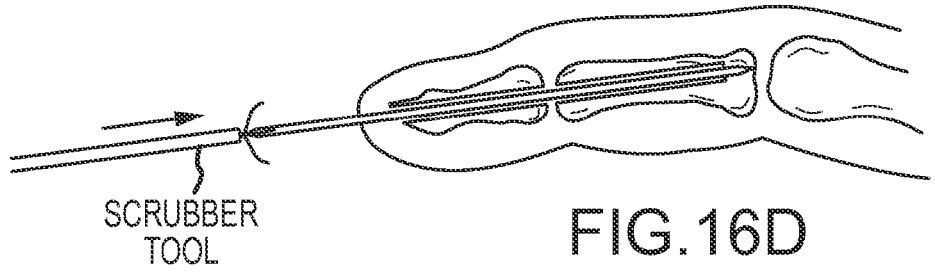
Figure 16E:
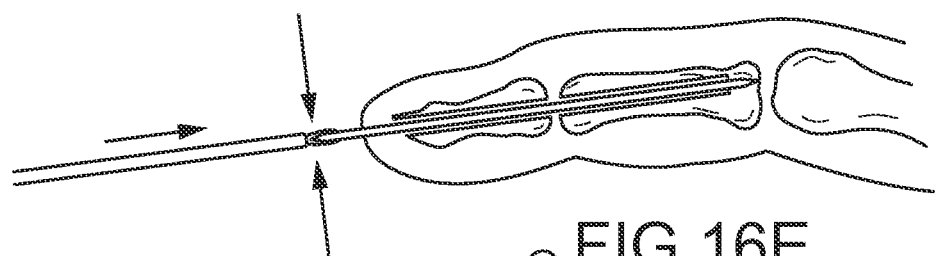
Figure 16F:
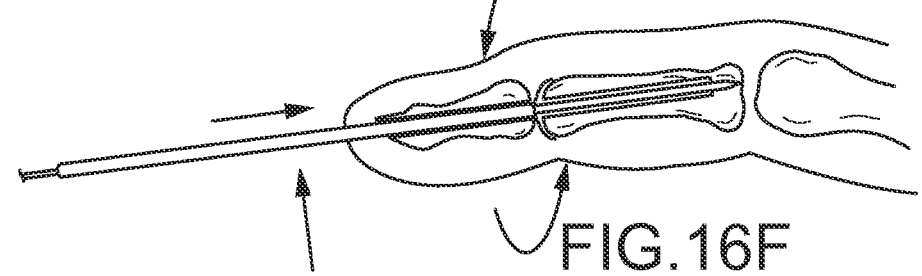

As shown in FIG. 16B, the finger is straightened to align the distal phalange and middle phalange, and the K-wire is inserted into the middle phalange. (Alternatively, the k-wire can just be drilled across the joint from the fingertip). In FIG. 16C, a cannulated drill bit is positioned over the K-wire and used to form an opening through the distal phalange and the medial phalange. FIGS. 16D-16F shows the drill bit removed, and a scrubber tool placed over the K-wire and moved into the opening to dislodge and remove cartilage or debris.

Figure 16G:
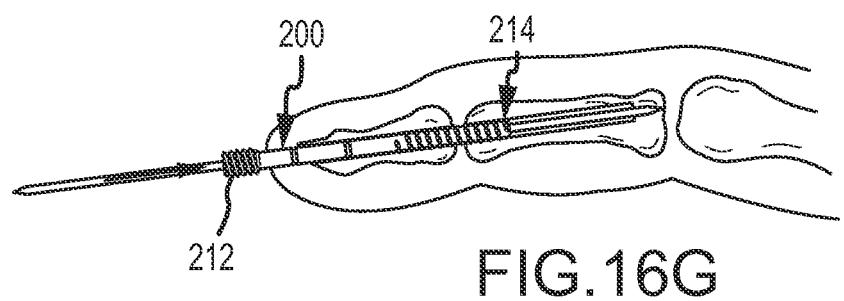
Figure 16H:
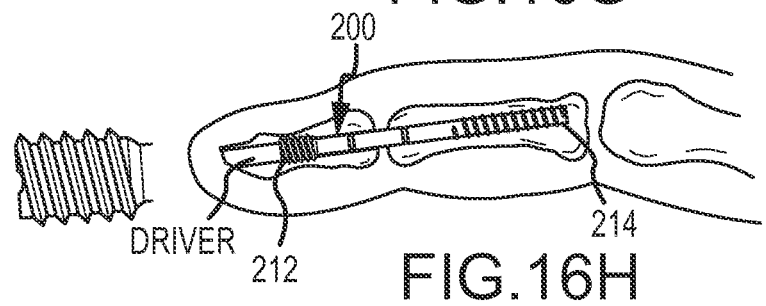

In FIG. 16G, device 200 is positioned on the K-wire by positioning the K-wire inside the cannula of the device 200. The K-wire may be inserted through the driving surface of device 200 and all the way through is then rotably threaded into the opening by a driver that fits over the K-wire and mates with the driving surface 220.

Figure 16I:
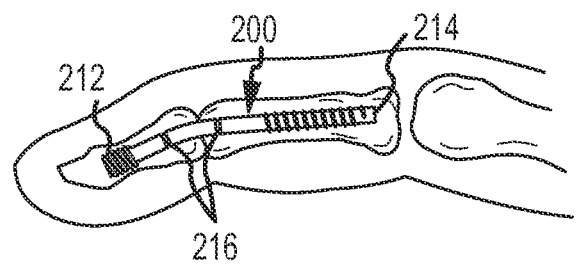

Once device 200 is in the proper position in the joint, which can be seen by medical personnel based on markings placed on device 200 that are visible using x-rays or other imaging techniques, the driver is removed. Then the K-wire is removed, which causes device 200 to return to its bent shape, and this causes the joint to move to a bent shape, as shown in FIG. 16I.

Figure 17:
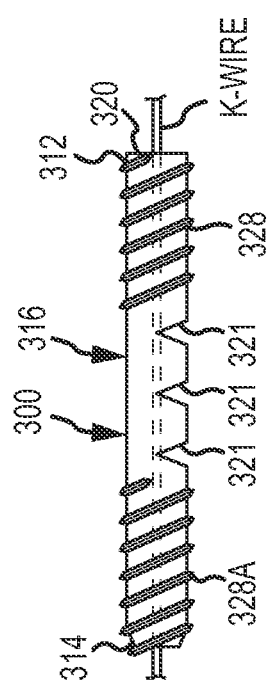
FIG. 17 depicts a side view of an alternate embodiment of a pre-bent device according to the invention in its straight position.
Figure 18:
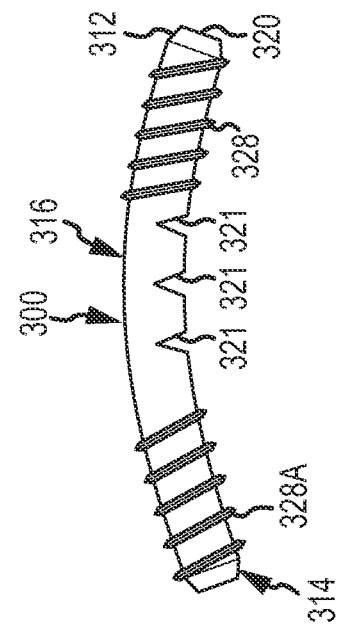
FIG. 18 shows a side view of the embodiment of FIG. 17 in its bent position.

Turning now to FIGS. 17 and 18, an alternate device 300 according to an aspect of the invention is shown. Device 300 is in all aspects the same as previously described device 200 except that it includes a plurality of notches 321 in shaft 316 that enable device 300 to be pre-bent. Device 300 also include an inner cannula (not shown) and is moved from its bent to a straight position when a K-wire is inserted through the cannula. This straightens device 200 from its pre-bent position to a straight position (as used herein in all embodiments, "straight" means relatively straight, which is not necessarily perfectly straight).

Device 300 is positioned into the bones of a joint to be fused in any suitable manner and can be positioned in the distal phalange and middle phalange in the manner previously described with respect to device 200. When a K-wire is inserted through the cannula of device 300, device 300 is moved from its bent to its straight position (the straight position is depicted in FIG. 17). When the K-wire is removed, device 300 moves from the straight position to its bent or relaxed position (the bent position is depicted in FIG. 18). In the preferred embodiment, device 300 is pre-bent to an angle of 15°, although any suitable angle may be utilized.

Figure 19:
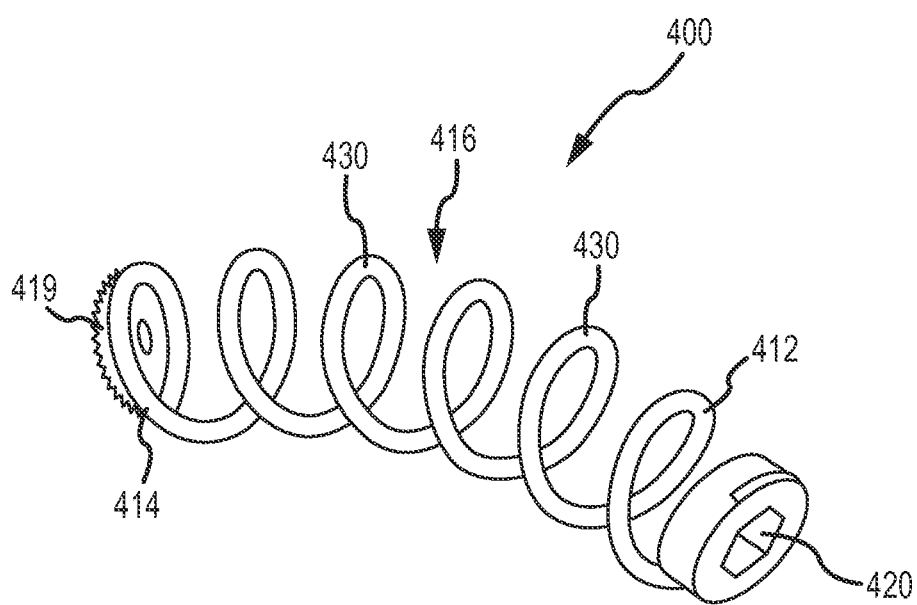
FIG. 19 is an alternate embodiment of a device according to the invention that utilizes coiled material to create a bend when the device is in its bent position.
Figure 20:
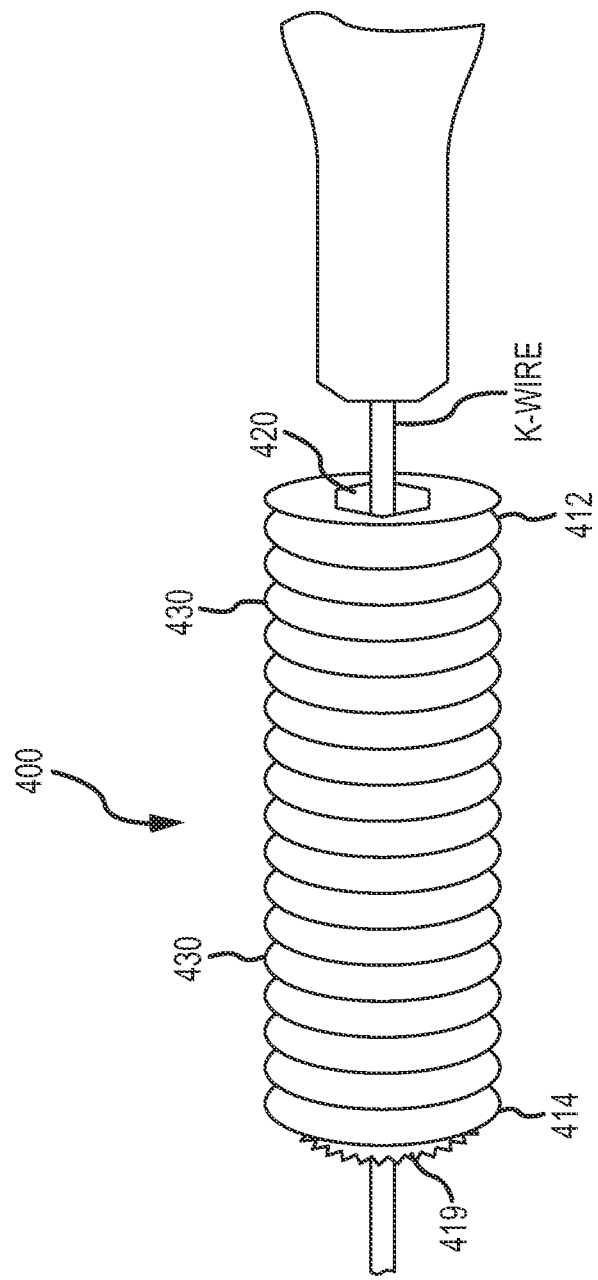
FIG. 20 shows a side view of the device of FIG. 19 in a straight position on a K-wire.

FIGS. 19 and 20 show an alternate device 400 according to an aspect of the invention. Device 400 has a coiled spring body 416 comprised of a continuous coiled structure 430. Body 416 is pre-bent to a suitable angle and is flexible enough to be moved from the bent position to a straight position when a K-wire is inserted through it, and rigid enough to maintain its bent position when positioned in a joint to be fused (under normal forces to which the joint would be subject).

Device 400 has a first end 412 that includes a driving surface 420 and a second end 414 that can include a cutting tip 419. In this embodiment tip 412 is preferably a metal cap or plate that attaches to body 416 and that includes driving surface 420. Driving surface 420 can have any of the previously defined configurations for a driving surface. End 414 is also preferably a metal cap or plate connected to body 416 and that includes the cutting tip 419. Cutting tip 419 can be of any suitable configuration, such as the configurations described for tips 219 and 319. End 412 and end 414 each have an opening suitable for receiving a K-wire or similar structure.

Device 400 can be positioned in a joint to be fused in any suitable manner and can be positioned in the distal phalang and medial phalange in the manner previously described with respect to device 200. When a K-wire is inserted through device 400, it moves device 400 from a bent to a straight position. When the K-wire is removed, device 400 moves form a straight position back to the bent position.

Figure 21:
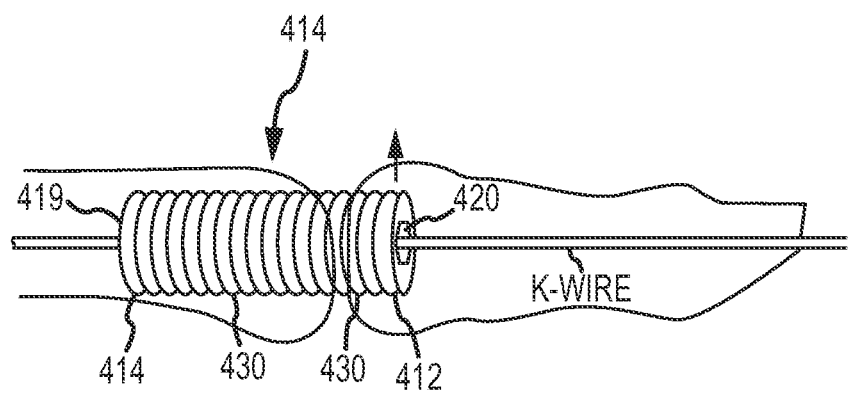
FIG. 21 shows the device of FIG. 20 positioned in a joint.

FIG. 20 shows device 400 pre-loaded onto a K-wire. The device is straightened with manual force and the k-wire is slipped down the cannulated canal in the device. The k-wire holds the spring device straight during insertion. A cannulated driver fits over the k-wire during insertion. FIG. 21 shows the device of FIG. 20 positioned in a finger joint. In this embodiment, the K-wire is first positioned in the joint by forming an opening in the joint as previously described, removing the K-wire used for forming the opening, placing the joint in a straight position and pushing the K-wire through the opening in the distal phalange and the middle phalange. Alternatively, the device can just be straightened and placed over the initial K-wire that is placed. The purpose of the initial K-wire is to confirm an intramedullary location and position of the K-wire so that subsequent drilling with a cannulated drill will be in the correct intramedullary position, and it is this same K-wire that can be used to install the device. The device is inserted over this K-wire and a driving tool, such as a screwdriver, designed to fit over the K-wire is used to screw the device into position.

Device 400 is then threaded in to the opening with first end 412 anchored into the distal phalange and second end 414 anchored into the middle phalange.

Figure 22:
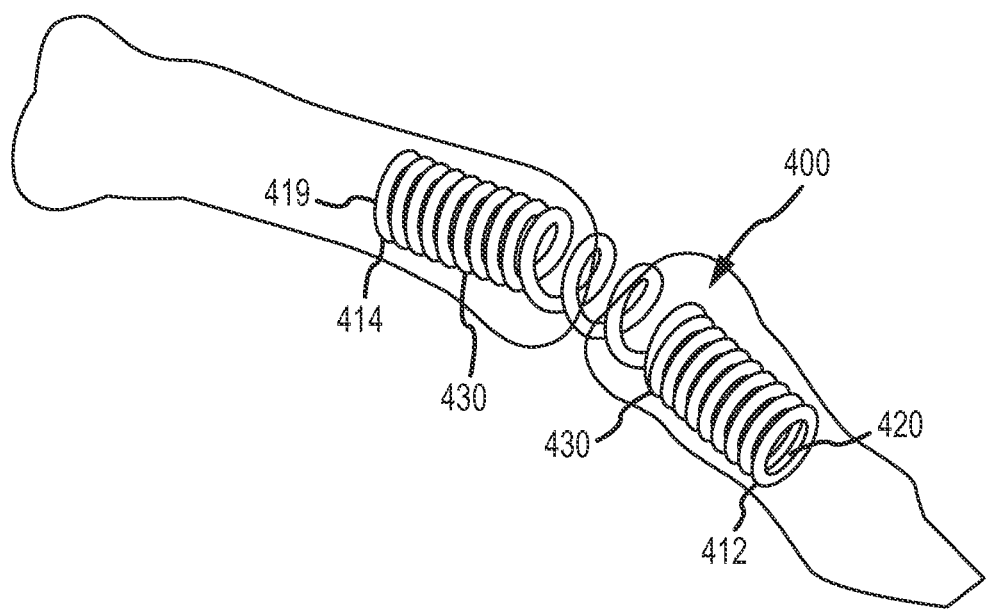
FIG. 22 shows the device of FIG. 21 in its bent position.

FIG. 22 shows device 400 positioned in a finger joint as described above with respect to FIG. 21 with the K-wire removed. This allows device 400 to move from a straight position to a bent position and moves the joint to a bent position.

Figure 23:
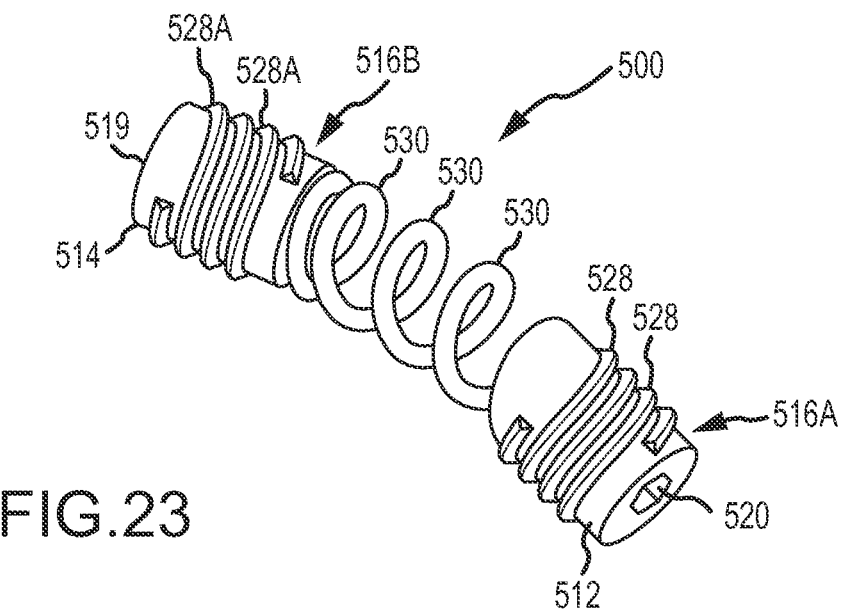
FIG. 23 shows a side view of an alternate device according to the invention.

FIG. 23 shows an alternate device 500 according to the invention. Device 500 has two shaft portions, a first, or proximal portion 516A, and a second, or distal portion 516B. First shaft portion 516A includes threads 528 and second shaft portion 516B includes threads 528A. It is preferred that threads 528 and 528A have the same pitch, spacing and outer diameter, but they may have different configurations.

First shaft portion 516A has a first end 512 and a driving surface 520. Driving surface 520 may be of any configuration previously described herein. Second shaft portion 516B has a second end 514 and preferably includes a cutting tip 519 (not shown). Cutting tip 519 may be of any suitable configuration, including those previously shown and described for tips 219, 319 and 419.

Device 500 also includes a continuous, coil spring center member 530. Center member 530 is pre-bent at a suitable angle and can be of the same material and have the same properties as previously described structure 416.

First shaft portion 516 and second shaft portion each have cannulas for receiving a K-wire. When a K-wire is received in device 500, device 500 moves from tis bent to a straight position. When the K-wire is removed, device 500 moves from a straight position back to its bent position.

Device 500 can be positioned in a joint to be fused in any suitable manner, including in the manner described above with respect to positioning device 400 in a finger joint.

Figure 24:
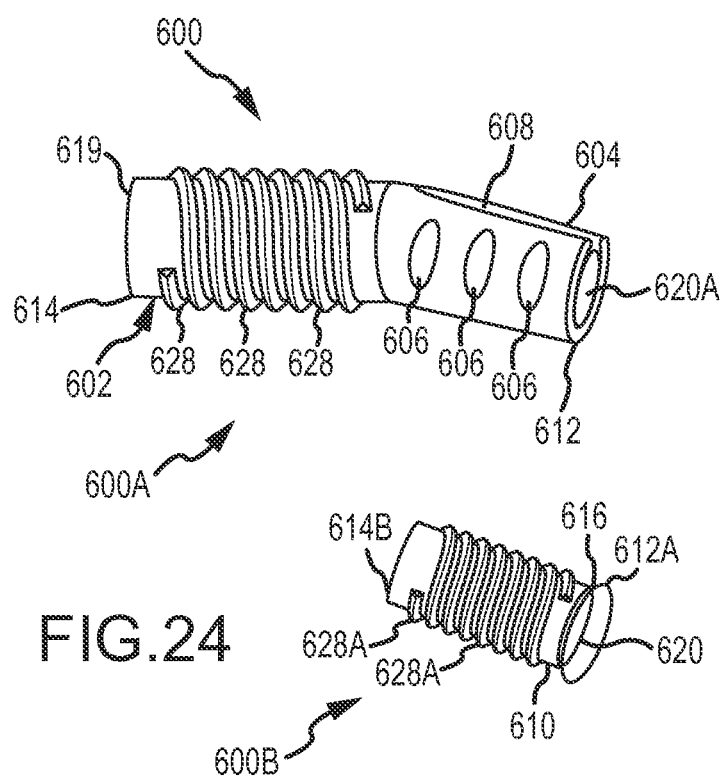
FIG. 24 shows an alternate embodiment of a device according to the invention.

FIG. 24 shows an alternate version of a pre-bent device that remains pre-bent while inserting it into a joint to be fused. Device 600 has a first body portion 600A and a second body portion 600B. First body portion 600B includes a first section 602 that as shown is preferably straight, and a second section 604 that is formed at a pre-bent angle relative first section 602.

First section 602 includes threads 628, a second end 614 and preferably includes a cutting tip 619 (not shown). Cutting tip 619 can have any suitable configuration including the ones described previously for other cutting tips. First section 602 also includes a cannula (not shown) extending therethrough, the cannula for receiving a K-wire.

Section portion 604 has a first end 612 and an opening 620A that leads to a cavity (not shown). Second portion 602B also has apertures 606 and optional internal threads (not shown) on the inner cavity wall for receiving second body portion 600B, as further described below. Alternatively, the inner cavity wall may not have threads.

Second portion 604 also has an open slot 608, which can be any opening capable of receiving a K-wire and permitting the K-wire to be inserted through the opening and straight through the cannula in first body portion 600A.

Second body portion 600B has a shaft 610, a first end 612A, a second end 614B and threads 628A. Second end 614B may be narrower than the outer diameter of the rest of shaft 610. End 612A as shown includes a flared portion 616. Driving surface 620 can have any suitable configuration, including any configuration previously described for a driving surface.

Figure 25:
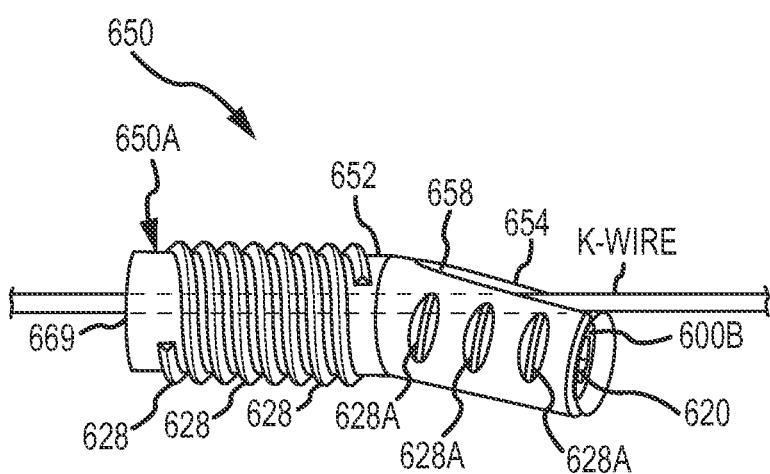
FIG. 25 shows the embodiment of FIG. 24 assembled.

In use, and as shown in FIG. 25, second body portion 600B is threaded into opening 620A of second portion 604 of first body portion 600A and into the cavity. Threads 628A may be received in internal threads in opening 620A, or may self-tap against the surface of opening 620A. As body portion 600B is threaded into the cavity, some of its threads 628 are exposed through openings 606 and the threads grip into the inner surface of the bone opening. Additionally, when the body portion 600B is threaded into the cavity, it can expand the second portion 604 to create a compression fit in the opening.

To be inserted into a joint, a K-wire is first inserted through the two bones forming the joint, such as described with respect to the phalanges shown in FIGS. 16-16I. The bones are then drilled to form an opening and scrubbed as previously described. Afterwards, first body portion is positioned over the K-wire in the opening and is threaded into place with first section 602 resting in the middle phalange. First section 604 is then positioned in the distal phalange, and the bend or angle between first section 602 and second section 604 is not altered to make first body portion 500A straight for insertion.

After first body portion 600A is positioned in the opening, the K-wire can be removed. Then second body portion 600B is positioned into opening 620A using a proper driving tool. As it is threaded into opening 620A, some of the threads 628A extend outward through openings 606 and grip the wall of the opening in the bone. This anchors device 600 inside of the distal phlange.

Figure 24A:
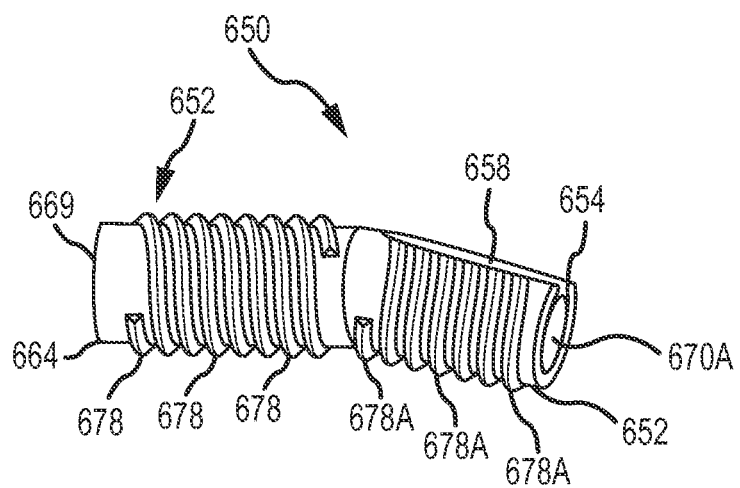
FIG. 24A shows an alternate embodiment of a device according to the invention.

FIG. 24A shows an alternate device 650 of the device 600 of FIGS. 24 and 25, except that device 650 does not include apertures 606. Device 650 has a first body portion 652 and a second body portion 654 that is formed at a pre-bent angle relative first body portion 652.

First body portion 652 includes threads 678, a second end 664 and preferably includes a cutting tip 669 (not shown). Cutting tip 669 can have any suitable configuration including the ones described previously for other cutting tips. First body portion 652 also includes a cannula (not shown) extending therethrough, the cannula for receiving a K-wire.

Section body portion 654 has a first end 662 and an opening 670A that leads to a cavity (not shown). Second body portion 654 also has optional internal threads (not shown) on the inner cavity wall for receiving portion 600B, as further described below. Alternatively, the inner cavity wall may not have threads.

Second body portion 654 also has an open slot 658, which can be any opening capable of receiving a K-wire and permitting the K-wire to be inserted through the opening and straight through the cannula in first body portion 652.

In use, portion 600B is threaded into opening 670A of second portion 654 of first body portion 654 and into the cavity. In this embodiment, the threads are not exposed through apertures 606, since there are no such apertures. Instead, threads 678A secure into the opening formed in the distal phalange. Portion 600B may still expand section 654 to create a compression fit in the opening.

Figure 25A:
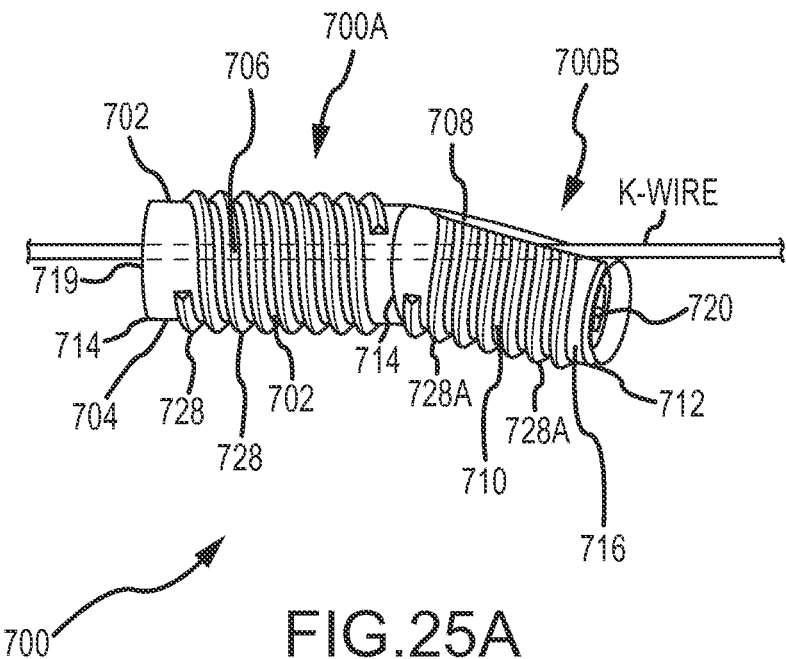
FIG. 25A shows the embodiment of FIG. 24A assembled.

FIG. 25A shows a pre-bent device that is one piece and remains pre-bent while inserting it into a joint to be fused. Device 700 has a first body portion 700A and a second body portion 700B. First body portion 700A as shown is preferably straight, and second section 700B is formed at a pre-bent angle relative first section 700A.

First body portion 700A includes a shaft 702, an outer surface 704, threads 728, a second end 714, and preferably includes a cutting tip 619 (not shown in FIG. 25). Cutting tip 719 can have any suitable configuration including the ones described previously for other cutting tips. Shaft 702 also includes a cannula 706 extending therethrough, the cannula for receiving a K-wire. Second portion 700B has a first end 712 and an opening 708.

Opening 708 can be any opening capable of receiving a K-wire and permitting the K-wire to be inserted through the opening and straight through the cannula in first body portion 700A.

Second body portion 700B has a shaft 710, a first end 712, a second end 714 and threads. End 712 as shown includes a flared portion 716. Driving surface 720 can have any suitable configuration, including any configuration previously described for a driving surface.

To be inserted into a joint, a K-wire is first inserted through the two bones forming the joint, such as described with respect to the phalanges shown in FIGS. 16-16I. The bones are then drilled to form an opening and scrubbed as previously described. Afterwards, first body portion 700A is positioned over the K-wire by positioning the K-wire through opening 708 and cannula 706. Device 700 is then threaded into the opening in the joint with first body portion 700A resting in the medial phlange. Second body portion 700B is positioned in the distal phlange, and the bend or angle between first body portion 700A and second body portion 700B is not altered to make device 700 straight for insertion.

The structure of device 700 makes it possible to thread it directly into a joint in its pre-bent shape utilizing a driving tool applied to driving surface 720. The K-wire inserted through opening 708, cannula 706 and into the opening in the joint reduces much of the eccentric movement (or wobble) of device 700 as it is being rotated, and enables a stable and safe insertion of device 700 into a joint.

Figure 26:
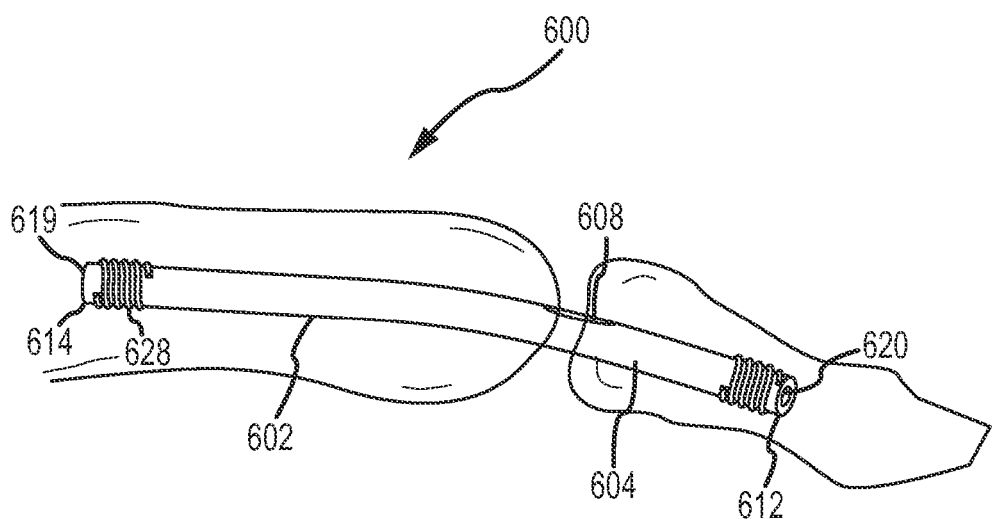
FIG. 26 shows the device of FIG. 25 positioned in a finger joint.
Figure 26A:
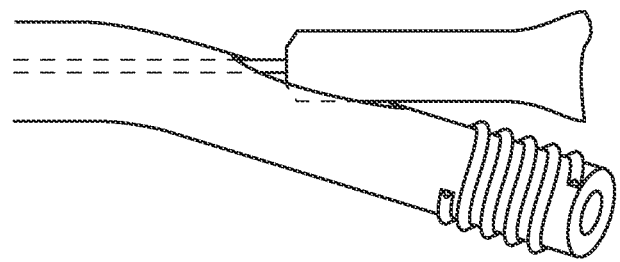
FIGS. 26A-26G shows a method of positioning a device according to the invention in a finger joint.
Figure 26B:
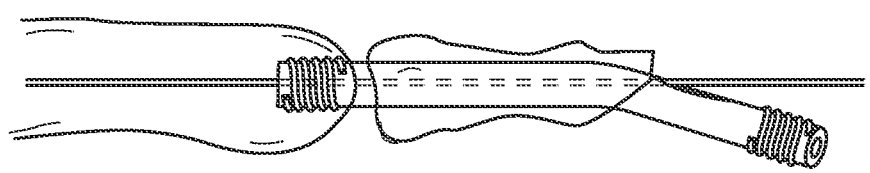
Figure 26C:
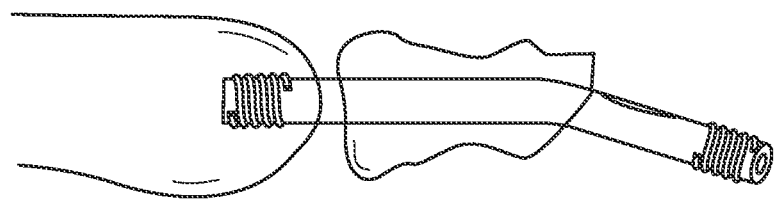
Figure 26D:
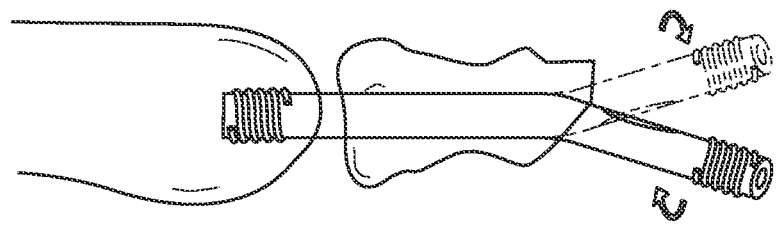
Figure 26E:
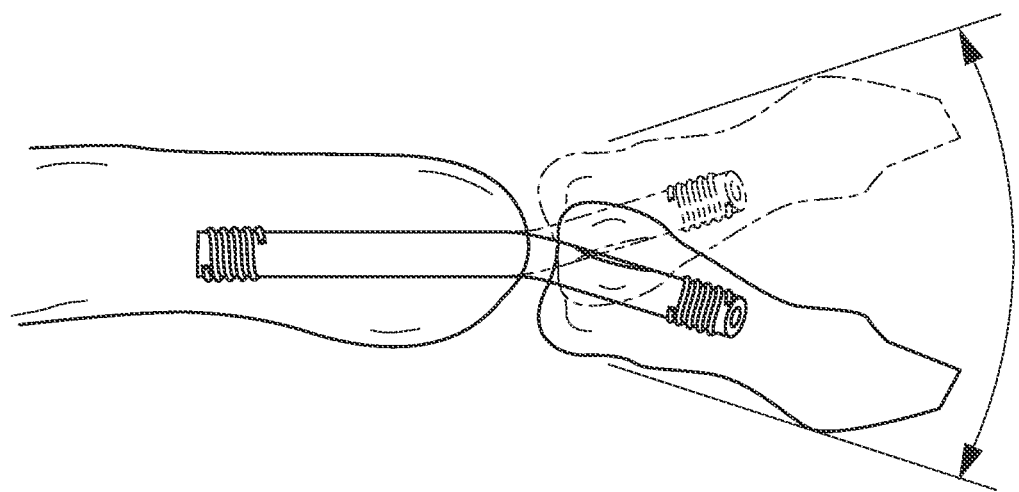
Figure 26F:
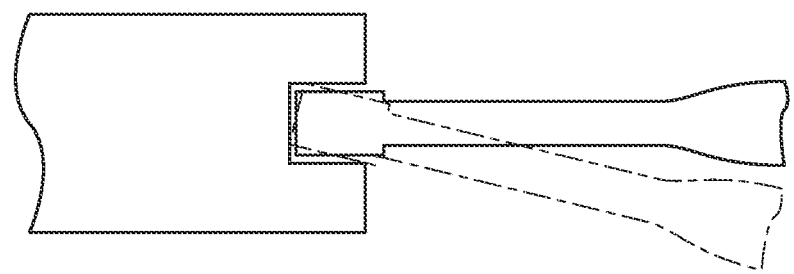
Figure 26G:
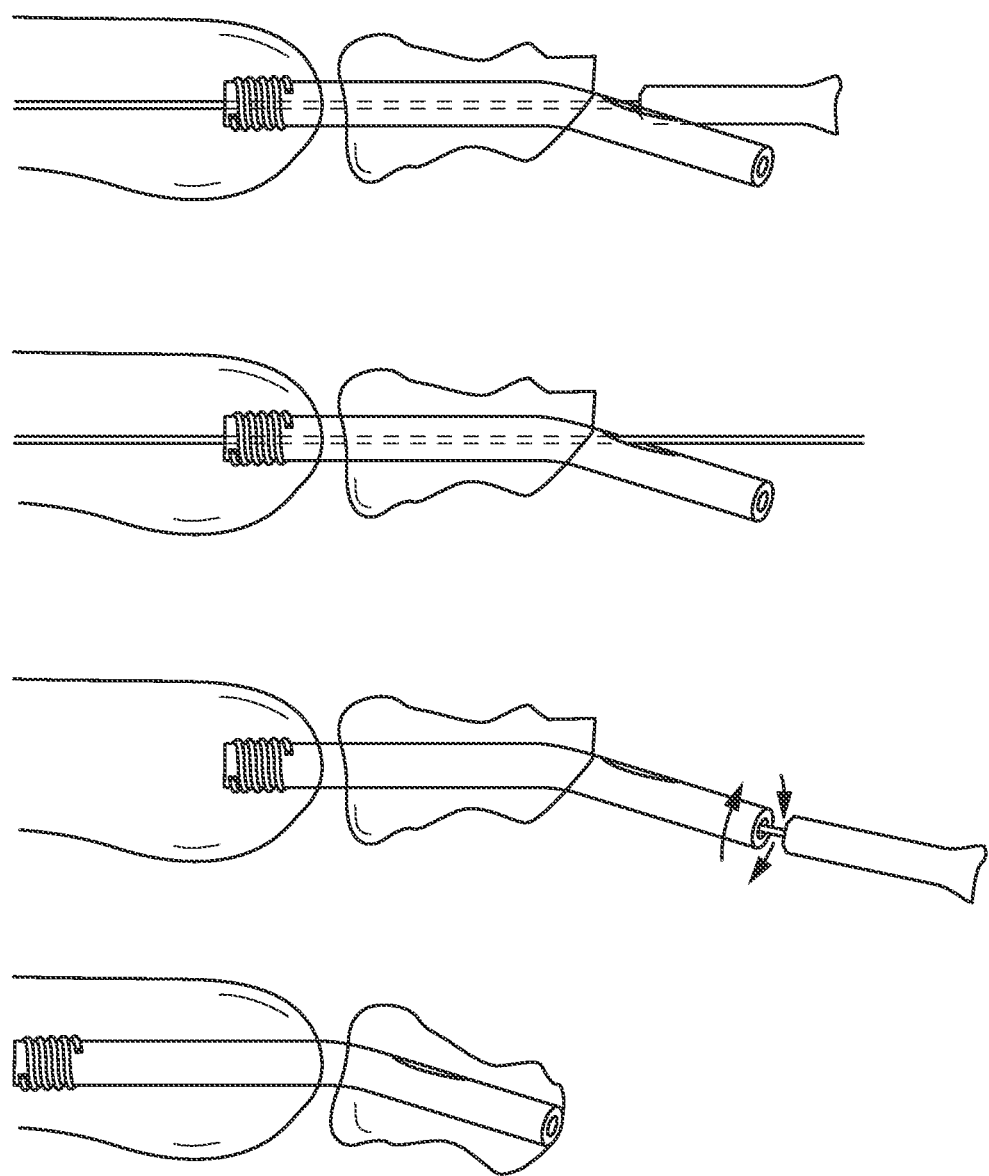

FIG. 26 shows device 700 positioned in a finger joint with portion 700A anchored in the medial phalange and portion 700B anchored in the distal phalange.

FIGS. 26A-26G show a bent screw that is inserted and positioned in the proper, pre-bent position relative to the joint. It is not straightened prior to insertion into the joint. This device could be device 600, device 650 or device 700. Furthermore, device 200 could first be pre-bent and inserted into a joint while in its bent position. The procedure for insertion is done in the manner as described herein. The resulting fusion has the fingertip positioned in a slightly flexed position. The threads 618 hold the device in the middle phalanx and the threads hold the device secure in the joint.

FIGS. 27-33 show embodiments of the invention that include structures to prevent twisting of a device once it is positioned in a joint in the bent position. In use over time, a patient may repeat the same movement many times and the bent fusion joint may move to the side. To help prevent this twisting movement structures may be included as part of any device according to the invention.

Figure 27:
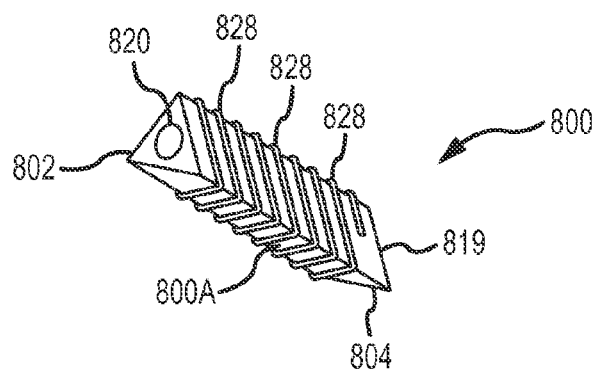
FIG. 27 shows a perspective view of an alternate device according to the invention.
Figure 28:
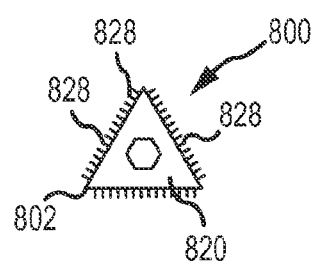
FIG. 28 shows a top view of the device of claim 27.

FIG. 27 shows a triangular, threaded device 800 that includes a first end 802, a second end 804, an outside surface 804, a cutting tip 819 (not shown), and a driving surface 820. Device 800 also has threads 828. Device 800 could be inserted in a straight or pre-bent position, and if inserted in the straight position, moved to a bent position either by applying force to it or by removing a K-wire as described herein. Device 800 is inserted into a joint in any suitable manner described shown or previously in this application. FIG. 28 is a top view of device 800.

Figure 29:
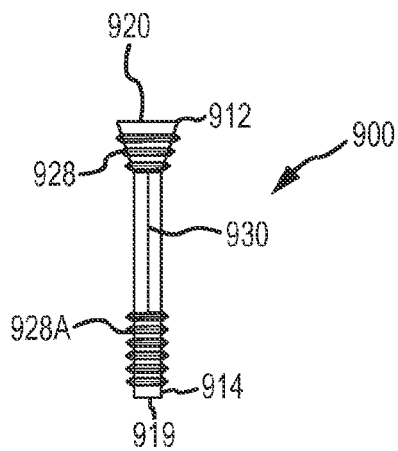
FIG. 29 shows a side view of an alternate device according to the invention in the straight position.
Figure 30:
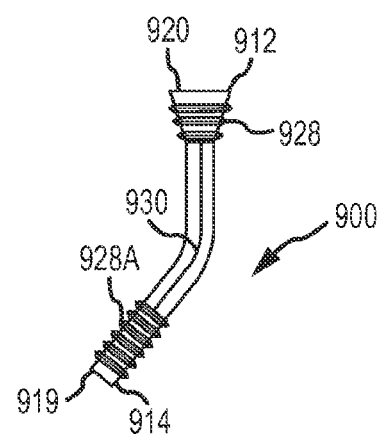
FIG. 30 shows the device of FIG. 29 in the bent position.

FIG. 29 shows a device 900 that is the same as previously described device 200 except that it includes one or more longitudinal ridges 930 that extend outward from device 900, preferably by about 0.5 to 2 mm, although any suitable distance may be used. The ridges 930 can be continuous or intermittent and be of any suitable length. Device 900 include a first end 912, a second end 914, a cutting tip 919 and threads 928 and 928A. Device 900 is inserted into a joint in the same manner as previously described for device 200, or inserted in any suitable manner. It may be inserted in the straight position and moved to the bent position, or inserted in the bent position. FIG. 30 shows device 900 in its bent position.

Figure 31:
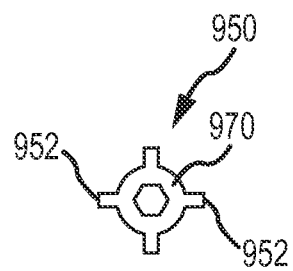
FIG. 31 shows a top view of an embodiment of the invention.

FIG. 31 is a top view of an alternate device 950. Device 950 has a first end with a driving surface 970 and projections 952. As shown there are four projections, but there could be any number of projections, and the projections preferably extend outward by 0.5 to 2 mm, although any suitable distance may be used. Such projections may be utilized on any device according to the invention. The projections may be positioned at any suitable position on a device, but it is most preferred that they are at the first end for ease of insertion.

Figure 32:
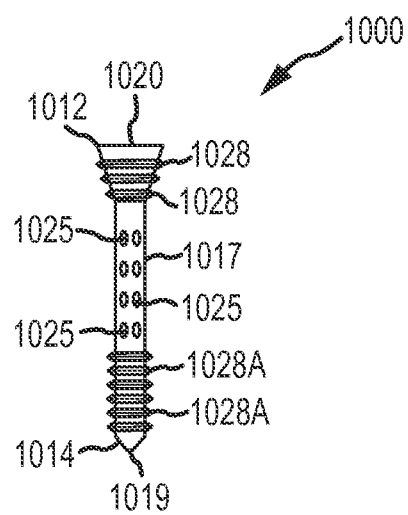
FIG. 32 shows a side view of an alternative embodiment according to the invention in the straight position.
Figure 33:
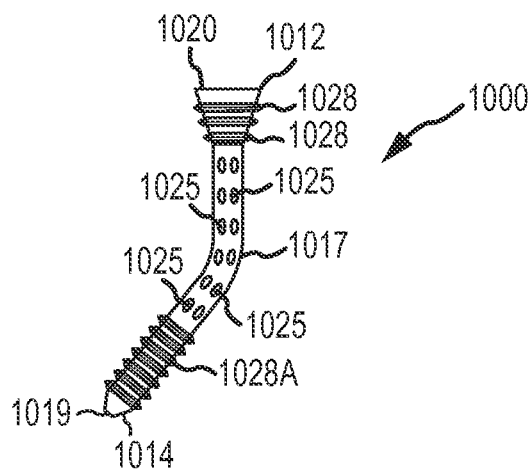
FIG. 33 shows the embodiment of FIG. 33 in the bent position.

FIG. 32 shows a device 1000 that is the same as previously described device 900 except that instead of one or more longitudinal ridges, it includes stipples 1025 to help prevent radial twisting. Device 1000 has a first end 1012, a second end 1014, an outer surface 1017, stipples 1025, a cutting tip 1019, threads 1028 and 1028A, and a driving surface 1020. Stipples 1025 preferably extend outward from surface 1017 by 0.5 to 2 mm, although any suitable distance may be used. The stipples 1025 can be spaced and positioned along device 1000 in any suitable manner. Device 1000 is inserted into a joint in the same manner as previously described for device 200, or inserted in any suitable manner. It may be inserted in the straight position and moved to the bent position, or inserted in the bent position. FIG. 33 shows device 1000 in its bent position.

Alternatively, a device according to the invention may have a plurality of the structures described herein for reducing or eliminating radial movement, or may include other structures for this purpose.

In another embodiment, the device may be S-shaped with two curves. The middle section comprises one bend, which is the major bend that creates an angled fusion. A second bend, which is a smaller bend, is positioned near the screw head and bends in a direction opposite the major bend. The second bend has aligns the driving tool so that the end of the device is generally straight relative the section that is positioned in the middle phalange.

The device may be made in different scales for different patient needs, such as sizing for children or adult patients. Having thus described some embodiments of the invention, other variations and embodiments that do not depart from the spirit of the invention will become apparent to those skilled in the art. The scope of the present invention is thus not limited to any particular embodiment. Unless expressly stated otherwise, the steps of any method described herein may be performed in any order capable of yielding the desired result.

What is claimed is:

1. A device for fusing a joint, the screw having a shaft, a first end, a second end, a center portion between the first end and the second end, a first anchoring portion juxtaposed to the first end, the device having a cannula extending therethrough for receiving a K-wire, the device having a first position wherein it is bent and a second position wherein it is angled, the screw being in the second position wherein the guide wire is in the cannula and the device being in the first position when the K-wire is not in the cannula.

2. The device of claim 1 wherein the cannula is in the center of the shaft.

3. The device of claim 1 that is comprised of one or more of nitinol stainless steel or titanium steel.

4. The device of claim 1 that has annular rings formed in the center portion wherein the annular rings permit the shaft to bend.

5. The device of claim 1 wherein the first anchoring portion has threads for being threadingly received in the joint.

6. The device of claim 1 wherein the second anchoring portion has threads for being threadingly received in the joint.

7. The device of claim 5 wherein the second anchoring portion has threads for being threadingly recurred in the joint.

8. The device of claim 1 wherein the device has a length and the center portion is between 40-80% of the length.

9. The device of claim 1 wherein the device has a length and the center portion is between 50-70% of the length.

10. The device of claim 1 wherein the first anchoring portion extends to the first end.

11. The device of claim 1 wherein the second anchoring portion extends to the second end.

12. The device of claim 1 wherein the second anchoring portion extends to the second end.

13. The device of claim 1 wherein the first end includes a driving surface for being driven by a tool.

14. The device of claim 13 wherein the driving surface is selected from the group consisting of surfaces the following: a flat-edge screw driver, a Phillips-head screw driver, a socket wrench, a Pozidriv, a Robertson driver, a tri-wing driver, a Torq-Set driver, a Spanner Head driver, a triple square driver, or an Allen wrenchs.

15. The device of claim 1 wherein the second end includes a cutting tip.

16. The device of claim 1 wherein the outer portion comprises an outer surface that is smooth and annular.

17. The device of claim 15 wherein the shaft narrows at the second end.

18. The device of claim 1 wherein the center portion comprises a coiled material.

19. The device of claim 18 wherein the center portion is a spring.

20. The device of claim 1 wherein the shaft, first end, second end, center portion, first anchoring portion and second anchoring portion are all comprised of the same material.

21. The device of claim 5 wherein there is a first length of threads on the second end and a second length of threads on the first end, the first length being greater than the second length.

22. The device of claim 21 wherein the first length is 1.5 to 2.5 times the second length.

23. The device of claim 21 wherein the second length is 1.5 to 3 times the first length.

24. A device for fusing a joint into a bent position, the device comprising a shaft with an outer surface, a first end, a second end, a first anchoring section juxtaposed the first end, a second anchoring portion juxtaposed the second end, and a center portion between the first anchoring portion and the second anchoring portion, the center portion having a bend in it, the bend having a proximal starting point and a distal ending point, and a cannula extending from an opening in the outer surface at the distal ending point and through the second end; the second anchoring portion has threads, and wherein there is a first length of the threads on the second end and a second length of threads on the first end, the first length being greater than the second length.

25. The device of claim 24 wherein the cannula extends at least partially through the center of the shaft.

26. The device of claim 24 that is comprised of one or more of nitinol, stainless steel and titanium steel.

27. The device of claim 24 wherein the first anchoring portion has threads for being threadingly received in the joint.

28. The device of claim 24 wherein the second anchoring portion has threads for being threadingly recurred in the joint.

29. The device of claim 24 wherein the device has a length and the center portion is between 40-80% of the length.

30. The device of claim 24 wherein the device has a length and the center portion is between 50-70% of the length.

31. The device of claim 24 wherein the first anchoring portion extends to the first end.

32. The device of claim 24 wherein the second anchoring portion extends to the second end.

33. The device of claim 31 wherein the second anchoring portion extends to the second end.

34. The device of claim 31 wherein the first end includes a driving surface for being driven by a tool.

35. The device of claim 24 that further includes a driving surface wherein the driving surface is selected from the group consisting of surfaces that can be driven by one of the following: a flat-edge screw driver, a Phillips-head screw driver, a socket wrench, Pozidriv, Robertson driver, tri-wing driver, Torq-Set driver, Spanner Head driver, triple square driver, or an Allen wrench.

36. The device of claim 24 wherein the second end includes a cutting tip.

37. The device of claim 24 wherein the center portion comprises an outer surface that is smooth and annular.

38. The device of claim 24 wherein the center portion comprises one or more radial grooves.

39. The device of claim 24 wherein the shaft, first end, second end, center portion, first anchoring portion and second anchoring portion are all comprised of the same material.

40. The device of claim 24 wherein the first length is 1.5 to 2.5 times the second length.

41. The device of claim 24 wherein the second length is 1.5 to 3 times the first length.

42. A device for fusing a joint into a bent position, the device comprising:
  (a) a first portion including a straight shaft having a first end, a first anchoring section juxtaposed the first end, and an angled shaft section attached to the straight shaft section, the angled section including a second end having an opening, and the first portion further including a cannula extending therethrough, and
  (b) a second portion including a straight shaft, a first end and a second end, the second end having a driving surface, the second portion being received in the angled section of the first portion.

43. The device of claim 42 wherein the opening has internal threads and the straight shaft of the second portion has an outer surface with threads, the second portion being threadingly received into the opening.

44. A method of fusing a joint into a bent position utilizing a device having a bent configuration, the device having a shaft with an outer surface, a first end having threads with a first thread diameter, a central portion with a bend, a second end having threads with a second thread diameter, the bend having a proximal ending point and a distal ending joint, the device further including a cannula that extends from an opening in the outer surface at the distal ending point, through the shaft and through the second end, the method comprising the steps of:
  (a) placing a K-wire through the bones of the joint to be fused;
  (b) forming an opening in the joint to be fused, the first opening having a diameter smaller than the first thread diameter and the second thread diameter;
  (c) positioning the K-wire into the cannula, and
  (d) screwing the second end of the device into the opening, which forces the joint into the bent position of the device.

45. The method of claim 44 wherein the screw includes a lumen, and that further includes the steps of:
  (a) to screwing the second end of the screw into the first opening; and removing the K-wire after the device is positioned in the joint.

46. The method of claim 44 or 45 wherein the first end of the device has threads and an outer thread diameter, the method further comprising the steps of:
  (a) forming a second opening in the joint to be fixed, the second opening having a diameter less than the second maximum thread diameter; and
  (b) screwing the first end of the screw into the second opening.

47. The method of any of claims 43-46 wherein the device is comprised of one or more of nitinol, stainless steel or titanium steel.

48. Any of the device may have antirotation mechanism consisting of ribs, texture, asymmetries in the entire device (square or triangle or other screw), or asymmetries in the head position.

* * * * *